(12) United States Patent
Ouchi

(10) Patent No.: US 7,497,826 B2
(45) Date of Patent: *Mar. 3, 2009

(54) ENDOSCOPIC HIGH-FREQUENCY KNIFE

(75) Inventor: Teruo Ouchi, Saitama (JP)

(73) Assignee: Hoya Corporation, Tokyo (JP)

( * ) Notice: Subject to any disclaimer, the term of this patent is extended or adjusted under 35 U.S.C. 154(b) by 444 days.

This patent is subject to a terminal disclaimer.

(21) Appl. No.: 10/922,956

(22) Filed: Aug. 23, 2004

(65) Prior Publication Data

US 2005/0049454 A1 Mar. 3, 2005

(30) Foreign Application Priority Data

| Aug. 27, 2003 | (JP) | ............................ 2003-302213 |
| Aug. 27, 2003 | (JP) | ............................ 2003-302214 |
| Aug. 27, 2003 | (JP) | ............................ 2003-302215 |
| Sep. 10, 2003 | (JP) | ............................ 2003-317624 |

(51) Int. Cl.
*A61B 1/00* (2006.01)

(52) U.S. Cl. ...................................... 600/127; 600/129

(58) Field of Classification Search ................ 600/127, 600/129, 104, 121; 606/41, 45–47
See application file for complete search history.

(56) References Cited

U.S. PATENT DOCUMENTS

| 4,311,144 | A | | 1/1982 | Harada |
| 5,976,073 | A | | 11/1999 | Ouchi |
| 6,019,720 | A | * | 2/2000 | Bito ............................ 600/123 |
| 6,086,583 | A | * | 7/2000 | Ouchi ........................... 606/41 |
| 6,190,384 | B1 | | 2/2001 | Ouchi |
| 6,224,611 | B1 | | 5/2001 | Ouchi |
| 6,299,612 | B1 | | 10/2001 | Ouchi |
| 6,416,490 | B1 | * | 7/2002 | Ellis et al. ....................... 604/22 |
| 6,780,178 | B2 | * | 8/2004 | Palanker et al. ................ 606/34 |
| 6,918,906 | B2 | * | 7/2005 | Long ............................. 606/41 |
| 6,932,812 | B2 | * | 8/2005 | Crowley et al. ................ 606/41 |
| 7,097,644 | B2 | * | 8/2006 | Long ............................. 606/41 |
| 7,137,981 | B2 | * | 11/2006 | Long ............................. 606/41 |
| 7,303,561 | B2 | * | 12/2007 | Ouchi ........................... 606/45 |
| 2003/0009085 | A1 | * | 1/2003 | Arai et al. ..................... 600/127 |
| 2005/0080412 | A1 | * | 4/2005 | Ouchi ........................... 606/45 |

FOREIGN PATENT DOCUMENTS

| JP | 2002-153484 | 5/2002 |
| JP | 2002-153485 | 5/2002 |

\* cited by examiner

*Primary Examiner*—Michael Peffley
*Assistant Examiner*—Victoria W Chen
(74) *Attorney, Agent, or Firm*—Greenblum & Bernstein, P.L.C.

(57) ABSTRACT

An endoscopic high-frequency knife includes immediately hood which is mounted to a distal end member fixed at a distal end of an endoscope to surround an end surface of the distal end member, an objective window being positioned on the end surface of the distal end member; a transparent hood portion which is formed on the hood to project forward from a portion of the hood in a vicinity of the end surface while being gradually curved inwards so as to cover the front of the end surface in a direction away from the end surface; and a high-frequency cutting electrode attached to the hood in a vicinity of a tip of the transparent hood portion, the high-frequency cutting electrode projecting forward from the transparent hood portion.

14 Claims, 36 Drawing Sheets

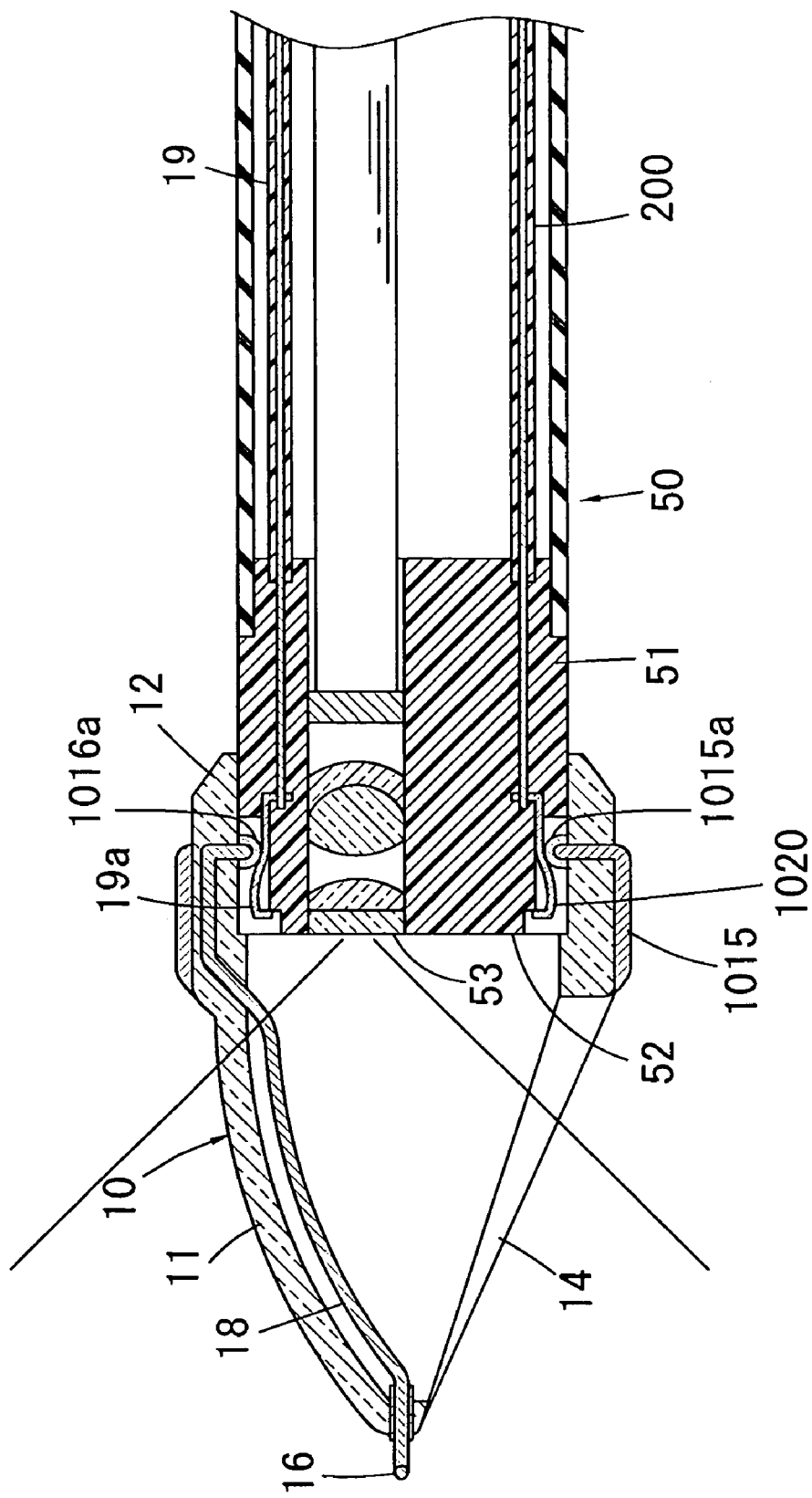

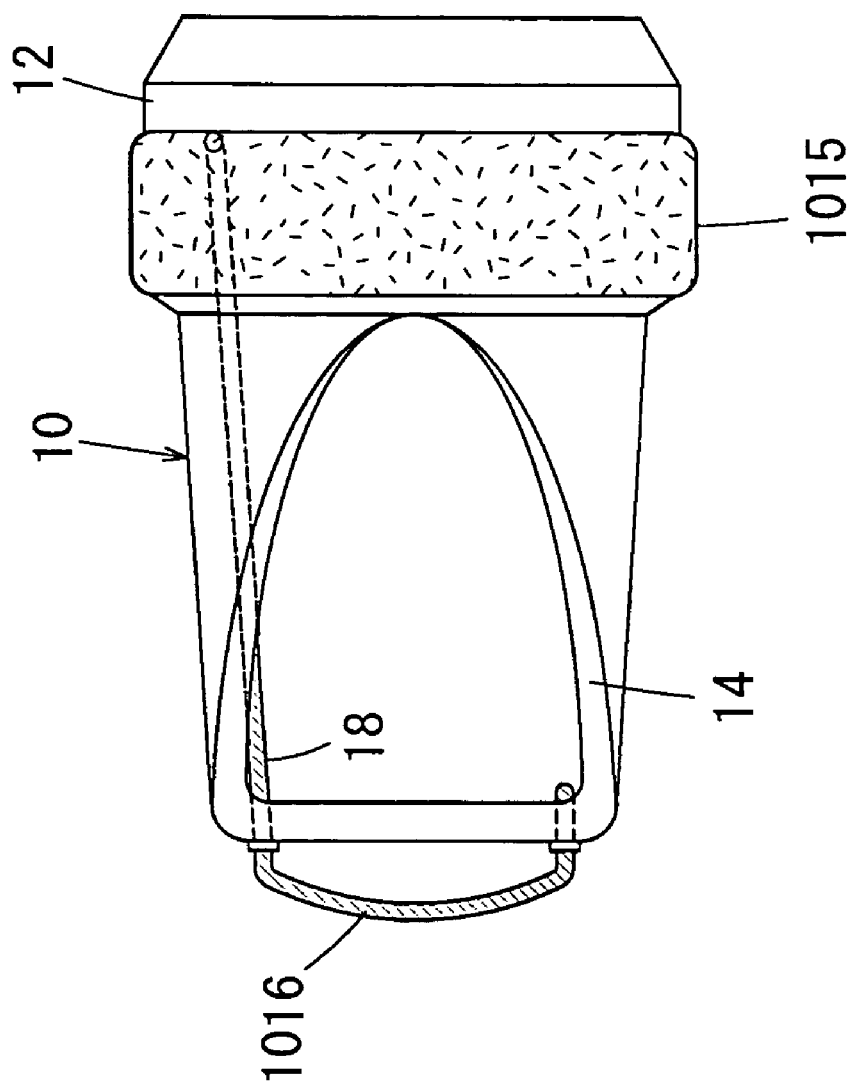

ND OSCOPIC HIGH-FREQUENCY KNIFE

BACKGROUND OF THE INVENTION

1. Field of the Invention

The present invention relates to an endoscopic high-frequency knife which is typically inserted trans-endoscopically into a body to dissect or resect mucosae of body tissues, and the like, via a passage of electric current through the knife.

2. Description of the Related Art

A typical endoscopic high-frequency knife is constructed and arranged so that a high-frequency cutting electrode is attached to a tip of an insulating flexible sheath which is inserted into a treatment tool insertion channel of an endoscope. In such an endoscopic high-frequency knife, it is difficult to determine the cutting depth because the cutting tip of the high-frequency cutting electrode sinks into the cut during an endoscopic surgical operation for dissecting a submucosa and the like. Therefore, there is a possibility of a body tissue being accidentally dissected excessively by an unintentional depth.

To prevent this problem from occurring, an endoscopic high-frequency knife in which the high-frequency cutting electrode is formed in a rod which is bent in a manner such that the tip of the rod is exposed from the surface of a mucosa, during the aforementioned endoscopic surgical operation for dissecting a submucosa, so that one can perform this endoscopic surgical operation while viewing the tip of the high-frequency cutting electrode on a monitoring screen has been proposed in Japanese Patent Publication No. 2002-153485.

However, even if the tip of the high-frequency cutting electrode, which is exposed from the surface of a mucosa during the endoscopic surgical operation for dissecting a submucosa, can be viewed on a monitoring screen with the an endoscopic high-frequency knife such as disclosed in the aforementioned Japanese Patent Publication, dissected surfaces of the submucosa which are in the process of being dissected by the high-frequency cutting electrode cannot be viewed in real time. Accordingly, it is not always the case that a medically-optimum prescribed range of submucosa can be dissected with such a conventional endoscopic high-frequency knife.

In a surgical operation for dissecting an affected area with a conventional endoscopic high-frequency knife, firstly the distal end of the endoscope is introduced into the body to a position suitable for surgical treatment for the affected area, subsequently the endoscopic high-frequency knife is projected from the tip of the insertion portion of the endoscope to precisely face the affected area, and finally the affected area needs to be dissected by a combination of a steering operation of the endoscope and a steering operation of an appropriate treatment tool. This procedure is very complicated.

SUMMARY OF THE INVENTION

The present invention provides an endoscopic high-frequency knife with which one can easily and safely dissect a medically-optimum prescribed area of submucosa, and the like, by a simple operation while viewing in real time dissected surfaces of the submucosa, and the like, which are in the process of being dissected by the high-frequency cutting electrode.

According to an aspect of the present invention, an endoscopic high-frequency knife is provided, including a hood which is mounted to a distal end member fixed at a distal end of an endoscope to surround an end surface of the distal end member, an objective window being positioned on the end surface of the distal end member; a transparent hood portion which is formed on the hood to project forward from a portion of the hood in a vicinity of the end surface while being gradually curved inwards so as to cover the front of the end surface in a direction away from the end surface; and a high-frequency cutting electrode attached to the hood in a vicinity of a tip of the transparent hood portion, the high-frequency cutting electrode projecting forward from the transparent hood portion.

It is desirable for the hood to be detachably attached to the distal end member.

The high-frequency cutting electrode can be formed in the shape of a wire which extends between two separate points in the vicinity of the tip of the transparent hood portion.

It is desirable for the high-frequency cutting electrode to extend linearly between the two separate points.

It is desirable for the high-frequency cutting electrode to be formed in the shape of an arc which bulges forward.

It is desirable for the high-frequency cutting electrode to be formed so that opposite ends of the high-frequency cutting electrode are extended rearward to opposite side surfaces of the transparent hood portion, respectively.

The high-frequency cutting electrode can be a conductive wire.

It is desirable for the hood to include a mounting portion which is mounted to the distal end member when the hood is attached to the distal end member, and a second conductive wire which extends from an end of the conductive wire is drawn out from the hood in a vicinity of the mounting portion of the hood through a space inside the transparent hood portion.

It is desirable for the second conductive wire to be drawn out from a rear end of the hood to extend rearward through the space inside the transparent hood portion.

It is desirable for the high-frequency cutting electrode to be attached to the hood in the vicinity of the tip of the transparent hood portion via at least one ceramic pipe.

It is desirable for the hood to have an opening on the opposite side of the hood from the transparent hood portion, the opening being shaped in such a manner that a portion of the hood between a point on the hood in a vicinity of a tip thereof and a point on a mounting portion of the hood that is mounted to the distal end member is cut off.

It is desirable for the opening to be positioned in front of the end surface of the distal end member, and to be shaped in such a manner that the portion of the hood is obliquely cut off.

It is desirable for the transparent hood portion to be shaped to fully cover the front of the end surface of the distal end member, the rear end of the opening being larger in a circumferential direction of the hood.

It is desirable for the endoscope to include an objective optical system provided behind the objective window. It is desirable for the hood to made of a transparent material.

In another embodiment, an endoscopic high-frequency knife is provided, including an attachment detachably attached to a distal end of an insertion portion of an endoscope; a transparent hood portion formed on the attachment to project obliquely forward so as to cover the front of the distal end of the insertion portion; and a high-frequency cutting electrode attached to the hood in a vicinity of a tip of the transparent hood portion to project forward therefrom.

In another embodiment, an endoscopic high-frequency knife is provided, including a hood which is mounted to a distal end member fixed at a distal end of an endoscope to surround an end surface of the distal end member, an objective window being positioned on the end surface of the distal end member; a transparent projecting portion which is formed on the hood to project forward from a portion of the hood in a vicinity of the end surface; and a high-frequency cutting electrode attached to the hood in a vicinity of a tip of the transparent projecting portion to project outwards therefrom.

It is desirable for the high-frequency cutting electrode to be formed in the shape of a wire which extends between two separate points in the vicinity of the tip of the transparent projecting portion.

It is desirable for the high-frequency cutting electrode to include a conductive wire.

It is desirable for the hood to include a mounting portion which is mounted to the distal end member when the hood is attached to the distal end member, and a second conductive wire which extends from an end of the conductive wire which is drawn out from the hood in a vicinity of the mounting portion of the hood through a space inside the transparent projecting portion.

It is desirable for the high-frequency cutting electrode to be attached to the hood in the vicinity of the tip of the transparent projecting portion via at least one ceramic pipe.

In another embodiment, an endoscopic high-frequency knife is provided, including a hood which is mounted to a distal end member fixed at a distal end of an endoscope to surround an end surface of the distal end member, an objective window being positioned at the end surface of the distal end member; a transparent cylindrical projecting portion which is formed on the hood to project forward from a portion of the hood in a vicinity of a whole outer edge of the end surface; and a high-frequency cutting electrode attached to a tip of the hood to project forward from a front end surface of the transparent cylindrical projecting portion so as to extend across a tip of the transparent cylindrical projecting portion.

It is desirable for a front end portion of the transparent cylindrical projecting portion to be formed narrower than another portion of the transparent cylindrical projecting portion, the high-frequency cutting electrode extending across the tip of the transparent cylindrical projecting portion in a direction of a major axis of the front end surface.

The front end surface of the transparent cylindrical projecting portion can include an oblique surface which is formed so that the high-frequency cutting electrode is positioned in a vicinity of a front end of the oblique surface.

The high-frequency cutting electrode can be formed in the shape of a wire which extends between two separate points in the vicinity of the tip of the transparent cylindrical projecting portion.

The high-frequency cutting electrode can be a conductive wire.

It is desirable for a second conductive wire which extends from an end of the conductive wire to be drawn out from the hood to extend rearward through a space inside the transparent cylindrical projecting portion.

In another embodiment, an endoscopic high-frequency knife is provided, including a hood which is mounted to a distal end member fixed at a distal end of an endoscope to surround an end surface of the distal end member, an objective window being positioned at the end surface of the distal end member; a transparent hood portion which is formed on the hood to project forward from a portion of the hood in a vicinity of the end surface while being gradually curved inwards so as to cover the front of the end surface in a direction away from the end surface; a high-frequency cutting electrode attached to the hood in a vicinity of a tip of the transparent hood portion to project forward therefrom; and a counter electrode attached to an outer peripheral surface of the hood. The high-frequency cutting electrode and the counter electrode serve as a pair of high-frequency electrodes.

It is desirable for the high-frequency cutting electrode to be formed in the shape of a wire which extends between two separate points in the vicinity of the tip of the transparent hood portion.

The high-frequency cutting electrode can be a conductive wire.

It is desirable for the counter electrode to be formed in a semi-cylindrical shape extending over an approximately half of a circumference of the hood. The high-frequency cutting electrode is positioned to be elongated in a direction substantially parallel to a straight line connecting diametrically opposite ends of the semi-cylindrical-shaped counter electrode.

It is desirable for the counter electrode to be formed in a cylindrical shape which circumferentially surrounds the hood.

It is desirable for a conductive wire which is electrically connected to at least one of the pair of high-frequency electrodes to extend rearwards from the hood.

The endoscopic high-frequency knife can include a first contact electrically connected to at least one of the pair of high-frequency electrodes, and positioned radially inside the hood. The endoscope includes a second contact electrically connected to at least one conductive cable provided inside the endoscope, and positioned on the distal end member. The first contact comes into contact with the second contact upon the hood being attached to the distal end member.

The present disclosure relates to subject matter contained in Japanese Patent Applications Nos. 2003-302213 (filed on Aug. 27, 2003), 2003-302214 (filed on Aug. 27, 2003), 2003-302215 (filed on Aug. 27, 2003) and 2003-317624 (filed on Sep. 10, 2003), which are expressly incorporated herein by reference in their entireties.

BRIEF DESCRIPTION OF THE DRAWINGS

The present invention will be discussed below in detail with reference to the accompanying drawings, in which:

FIG. 35 is a cross sectional view of a tenth embodiment of the endoscopic high-frequency knife according to the present invention, and the distal end of an endoscope to which the endoscopic high-frequency knife is attached; and FIG. 36 is a bottom view of the tenth embodiment of the endoscopic high-frequency knife shown in FIG. 35.

DESCRIPTION OF THE PREFERRED EMBODIMENTS

[First Embodiment]

Figure 1:
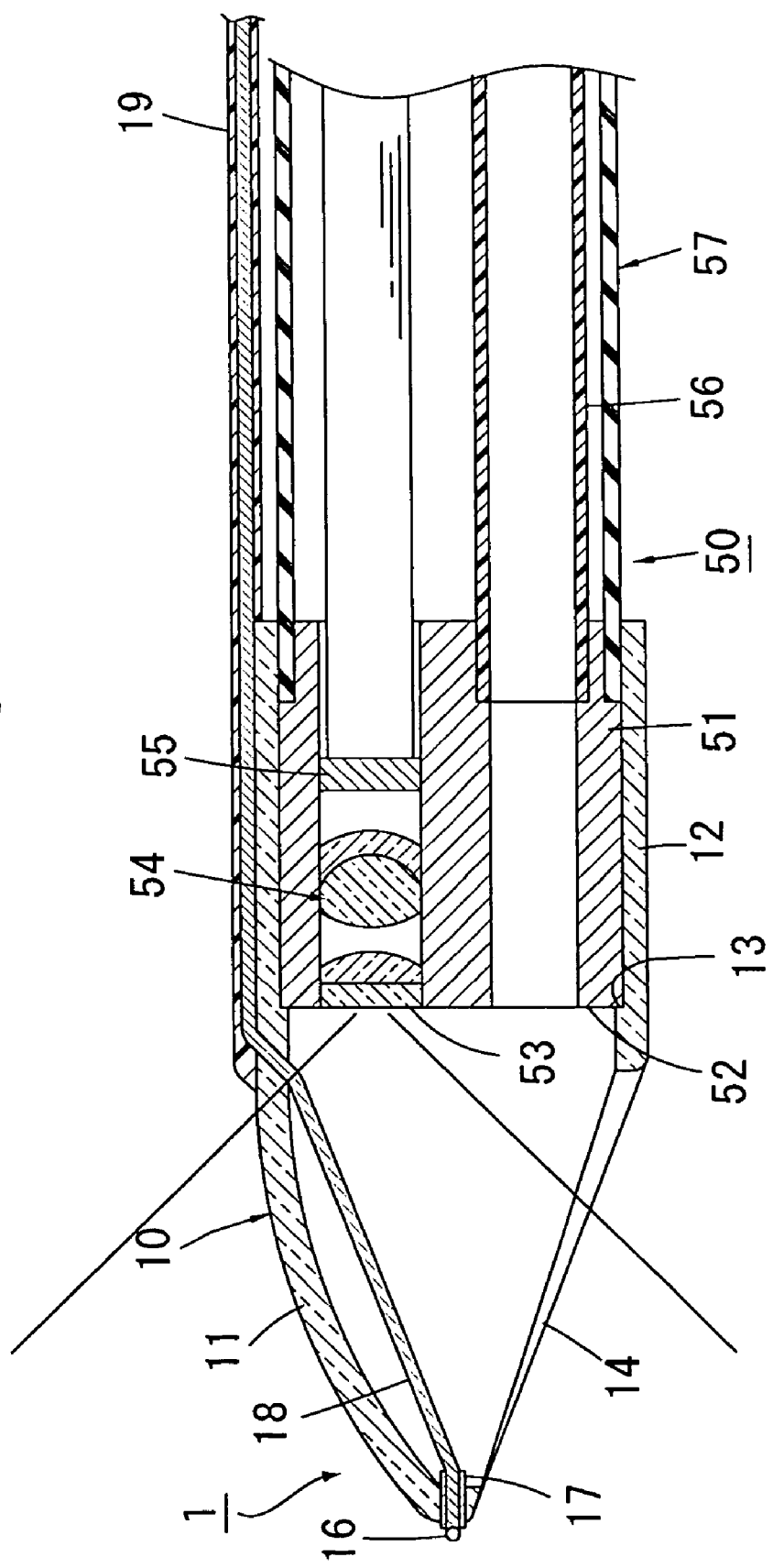
FIG. 1 is a cross sectional view of a first embodiment of an endoscopic high-frequency knife according to the present invention, and the distal end of an endoscope to which the endoscopic high-frequency knife is attached.

In the first embodiment, as shown in the cross sectional view in FIG. 1, an endoscopic high-frequency knife 1 has a transparent hood (attachment) 10 which is mounted to a cylindrical distal end member 51 fixed at a distal end of an endoscope 50 to surround an end surface 52 of the cylindrical distal end member 51, an objective window 53 being positioned on the end surface 52 of the cylindrical distal end member 51; a transparent hood portion 11 which is formed on the transparent hood 10 to project forward. from a portion of the transparent hood 10 in the vicinity of the end surface 52 while being gradually curved inwards so as to cover the front of the end surface 52 in a direction away from the end surface; and a high-frequency cutting electrode (conductive wire) 16 attached to the transparent hood 10 in the vicinity of a tip of the transparent hood portion 11 to project forward therefrom.

Figure 2:
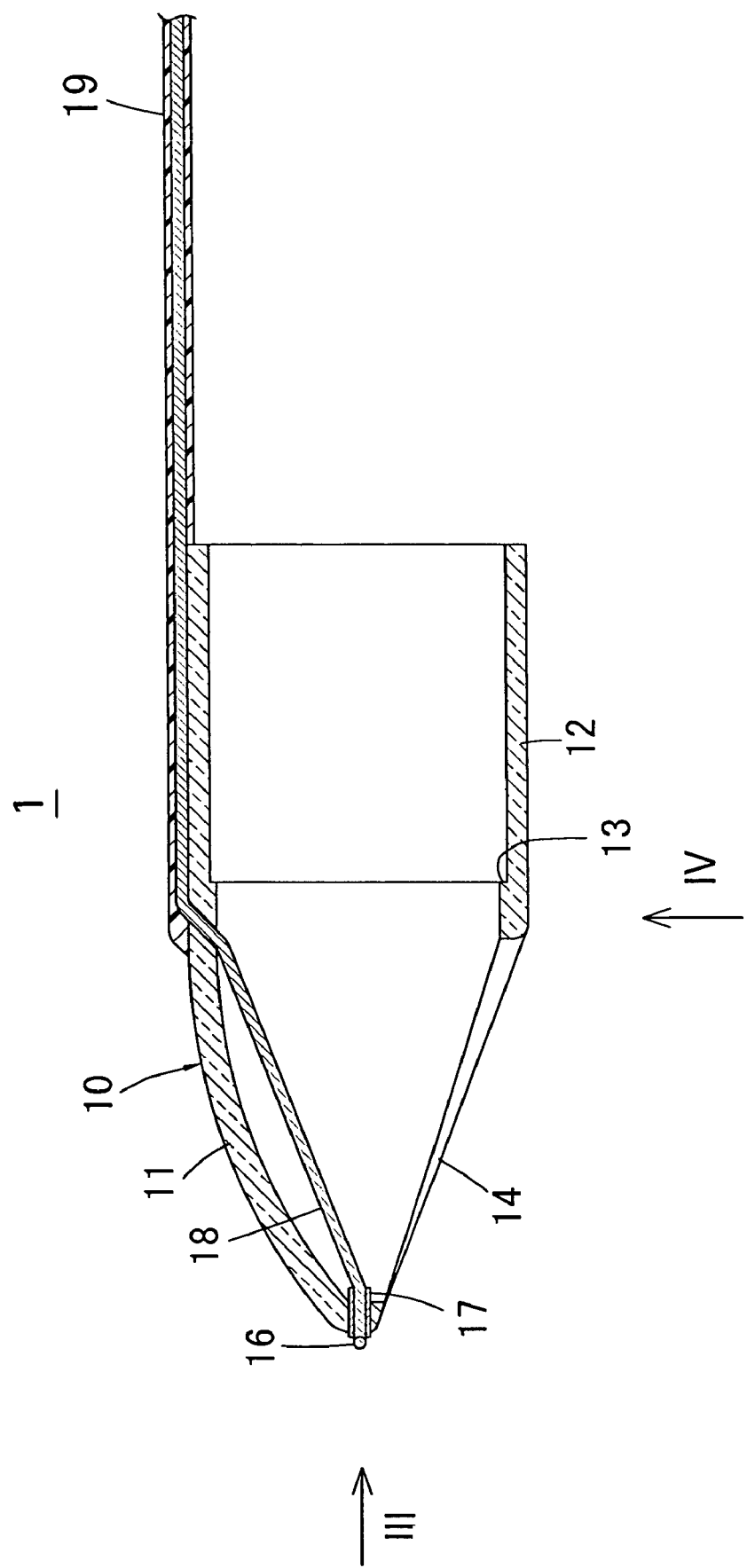
FIG. 2 is a cross sectional view of the first embodiment of the endoscopic high-frequency knife shown in FIG. 1.
Figure 3:
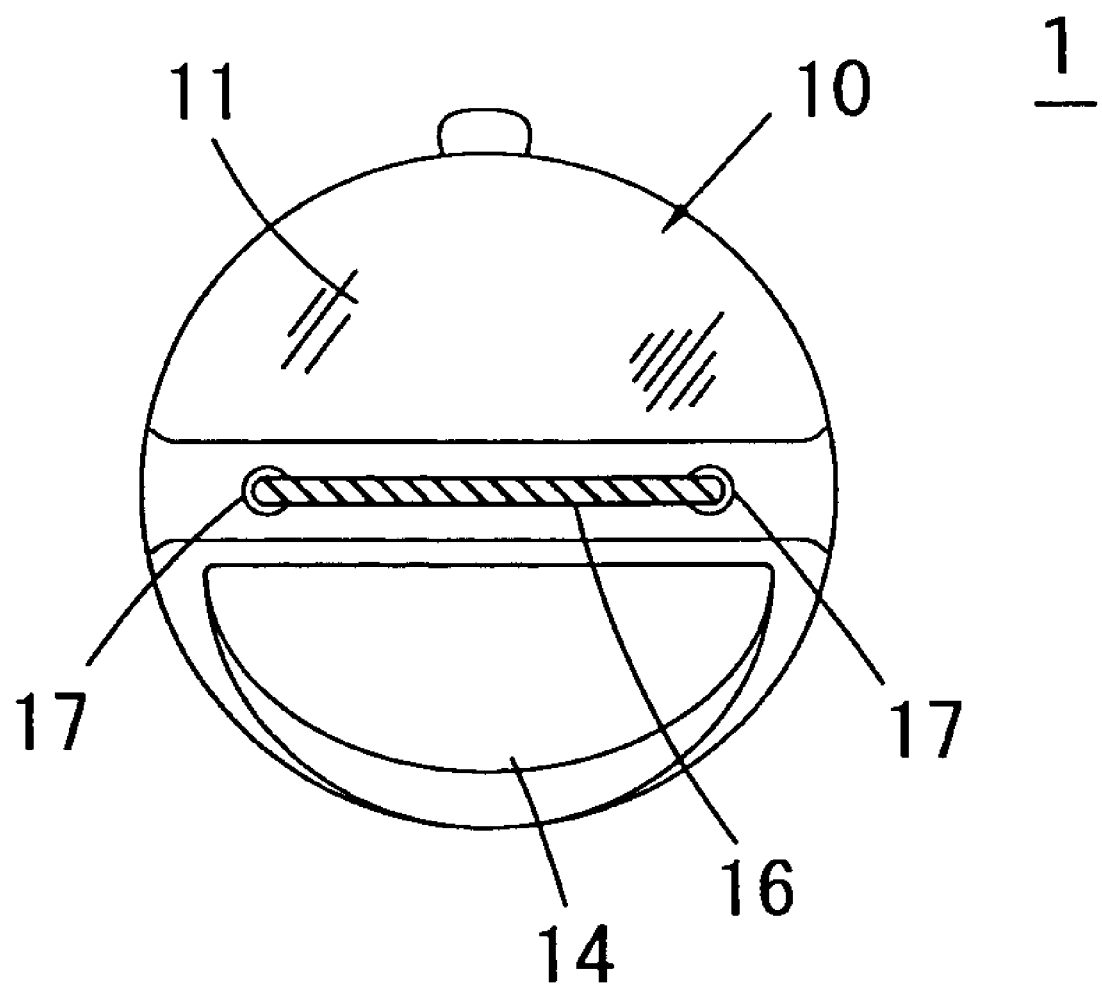
FIG. 3 is a front view of the first embodiment of the endoscopic high-frequency knife, viewed in the direction of an arrow III shown in FIG. 2.
Figure 4:
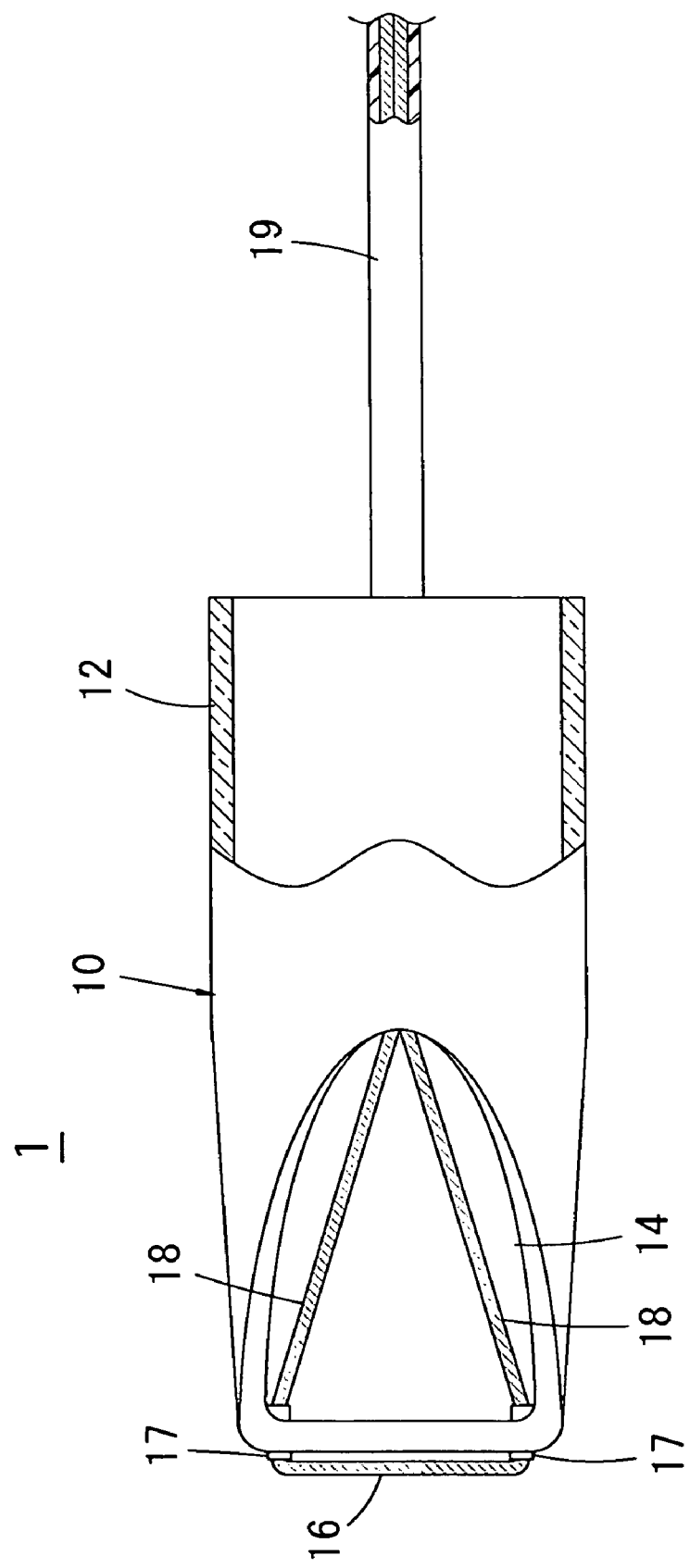
FIG. 4 is a bottom view, partly in cross section, of the first embodiment of the endoscopic high-frequency knife, viewed in the direction of an arrow IV shown in FIG. 2.

FIG. 1 shows a state where the endoscopic high-frequency knife 1 is attached to the distal end of the endoscope 50. FIG. 2 is a cross sectional view of the endoscopic high-frequency knife 1, FIG. 3 is a front view of the endoscopic high-frequency knife 1, viewed in the direction of an arrow III shown in FIG. 2, and FIG. 4 is a bottom view, partly cross section, of the endoscopic high-frequency knife 1, viewed in the direction of an arrow IV shown in FIG. 2.

The endoscope 50 is a front-viewing type in which an objective window 53 for viewing the front of the distal end of the endoscope 50 is positioned at an end surface 52 of a cylindrical distal end member 51 that forms a front end of an insertion portion of the endoscope 50. Note that the endoscope 50 can be an oblique-front-viewing type.

A light bundle of an object which is passed through the objective window 53 is focused on an imaging surface of a solid-state image pick-up device (e.g., a CCD image sensor) 55 (or an end surface of an image guide made of an optic fiber bundle) via an objective optical system 54. The endoscope 50 is provided with a treatment tool insertion channel 56 through which various treatment tools such as a retrieval basket are introduced into the body. The front end opening of the treatment tool insertion channel 56 is open at the end surface 52 of the distal end member 51.

The insertion portion of the endoscope 50 is generally formed as a flexible tube which can be freely bent by an external force, while a distal end portion of the insertion portion of the endoscope 50 in the vicinity of the distal end member 51 is made as a steerable bendable portion 57 which can be steered to bend in any direction by controlling a steering device (not shown) provided at a proximal end of the insertion portion of the endoscope 50. The structure of this steering mechanism is well-known in the art, and accordingly, a detailed description about the steering mechanism is omitted.

The transparent hood 10 is detachably attached to the distal end member 51 in such a manner to surround the end surface 52 of the cylindrical distal end member 51 of the endoscope 50. The transparent hood 10 can be made of a transparent resin such as a transparent acrylic resin or a transparent polycarbonate resin.

A major part of the transparent hood 10 is formed as a hood portion 11 which projects forward from a portion of the transparent hood 10 in the vicinity of the end surface 52 of the distal end member 51 and gradually curves inwards so as to cover the front of the end surface 52 in a direction away from the end surface 52. The transparent hood 10 will do if at least the hood portion 11 is optically transparent.

A rear portion of the transparent hood 10 behind the hood portion 11 is formed as a mounting portion 12 having a cylindrical shape which can be removably fitted on an outer peripheral surface of the distal end member 51. The installation position of the transparent hood 10 on the distal end member 51 is determined by contact of the end surface 52 of the distal end member 51 with a stepped portion 13 formed on an inner peripheral surface of the mounting portion 12.

In the first embodiment of the endoscopic high-frequency knife, the transparent hood 10 is prevented from coming off the distal end member 51 over the course of time by fitting the mounting portion 12 firmly and resiliently on the distal end member 51. Note that a device for preventing the transparent hood 10 from coming off the distal end member 51, e.g., an engaging device consisting of an engaging projection and an engaging groove which are engageable with each other, can be provided between the transparent hood 10 and the distal end member 51.

The hood portion 11 of the transparent hood 10 is formed to have a curved surface which is slightly convexed forwards. As shown in FIG. 4, the tip of the hood portion 11 is formed to have a laterally straight surface to which a high-frequency cutting electrode 16 is attached to project forward from the laterally straight surface.

Accordingly, the conditions of the high-frequency cutting electrode 16 and the periphery thereof can be viewed from the objective window 53 through the transparent hood portion 11. It is desirable that the depth of field of the objective optical system 54 be determined so as to be suitable for such an optical arrangement. The usability of the endoscopic high-frequency knife 1 becomes greatest if the distance from the objective window 53 to the high-frequency cutting electrode 16 is slightly over 10 mm.

The high-frequency cutting electrode 16 is made of a conductive wire. The endoscopic high-frequency knife 1 is provided, at the tip of the hood portion 11 in the vicinity of laterally-opposite ends thereof, with two heat-resistant pipes 17 made of ceramics, which are positioned laterally apart from each other and each of which extends through the tip of the hood portion 11 in a forward/rearward direction of the transparent hood 10. The opposite ends of the high-frequency cutting electrode 16 are inserted into the two heat-resistant pipes 17 from the front ends thereof, respectively, so that the high-frequency cutting electrode 16 is attached to the tip of the hood portion 11 while remaining tightly stretched between the front ends of the two heat-resistant pipes 17.

Two conductive wires 18 which extend from the opposite ends of the high-frequency cutting electrode 16 come out from the rear ends of the two heat-resistant pipes 17, respectively, to be drawn out from the transparent hood 10 in the vicinity of the mounting portion 12 through the space inside the hood portion 11, and are subsequently extended rearward as a conductive cable (two-wire cable) 19.

Since the high-frequency cutting electrode 16 of the present embodiment of the endoscopic high-frequency knife 1 according to the present invention is a monopole type, the high-frequency cutting electrode 16 does not necessarily have to be provided with two of the conductive wires 18. Namely, for instance, one end of the high-frequency cutting electrode 16 can be attached to the associated heat-resistant pipe 17.

The transparent hood 10 is provided, on the opposite side of the hood portion 11 (on a portion of the transparent hood 10 below the hood portion 11 as viewed in FIG. 2), with an opening 14 which is shaped in such a manner that a portion of the transparent hood 10 between a point on the transparent hood 10 in the vicinity of the tip thereof and a point on the mounting portion 12 of the transparent hood 10 is obliquely cut off. Since the opening 14 is open toward the front of the treatment tool insertion channel 56, a treatment tool and the like which is inserted into the treatment tool insertion channel 56 from its insertion opening (not shown) can be made to project through the opening 14.

Figure 5:
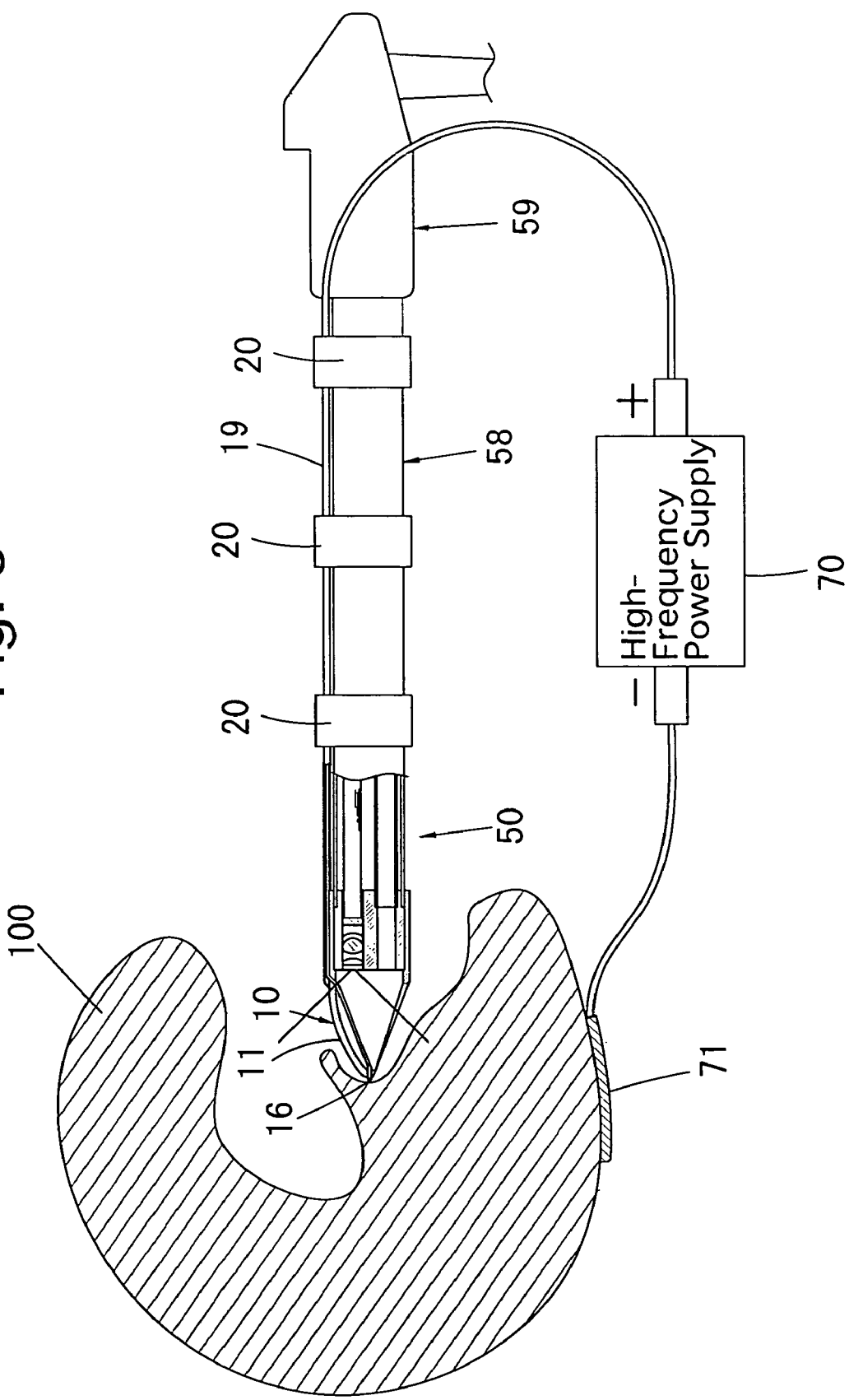
FIG. 5 is a schematic diagram showing a state where the first embodiment of the endoscopic high-frequency knife is set to dissect a submucosa of a body tissue with the endoscopic high-frequency knife.

FIG. 5 shows a state where the first embodiment of the endoscopic high-frequency knife 1 is set to dissect a submucosa of a body tissue 100 with the endoscopic high-frequency knife 1. In this state, the conductive cable 19 which is drawn from the transparent hood 10 to extend rearward is fixed on an insertion portion 58 of the endoscope 50 along a lengthwise direction thereof by fixing bands 20 so that the rear end of the conductive cable 19 is connected to a positive terminal of a high-frequency power supply 70. A counter electrode 71 which is in contact with a large area of an outer surface of the body tissue 100 is connected to a negative terminal of the high-frequency power supply 70. The reference numeral 59 shown in FIG. 5 designates an operational portion of the endoscope 50.

Figure 6:
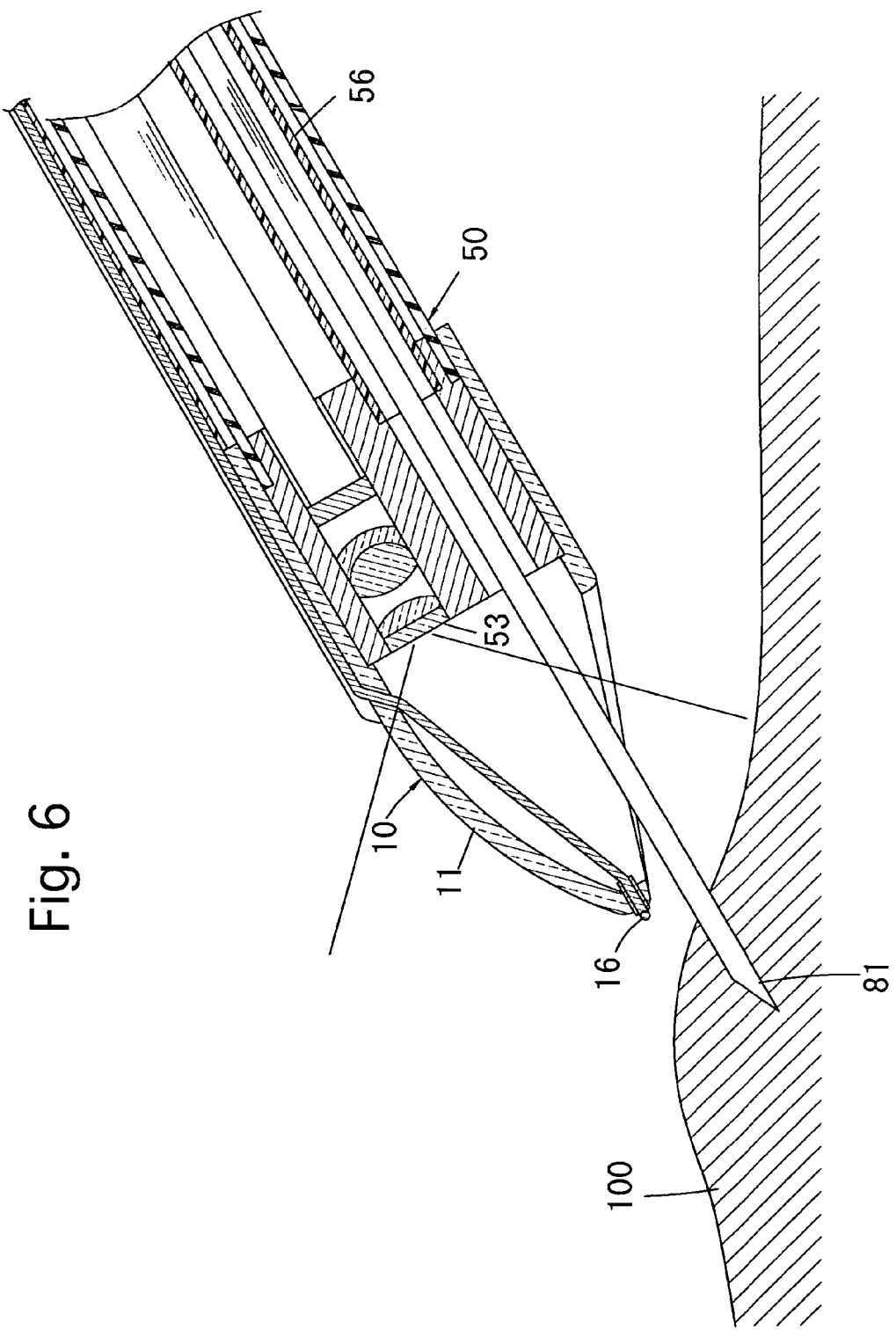
FIG. 6 is a cross sectional view of the first embodiment of the endoscopic high-frequency knife, showing an operational state thereof.
Figure 7:
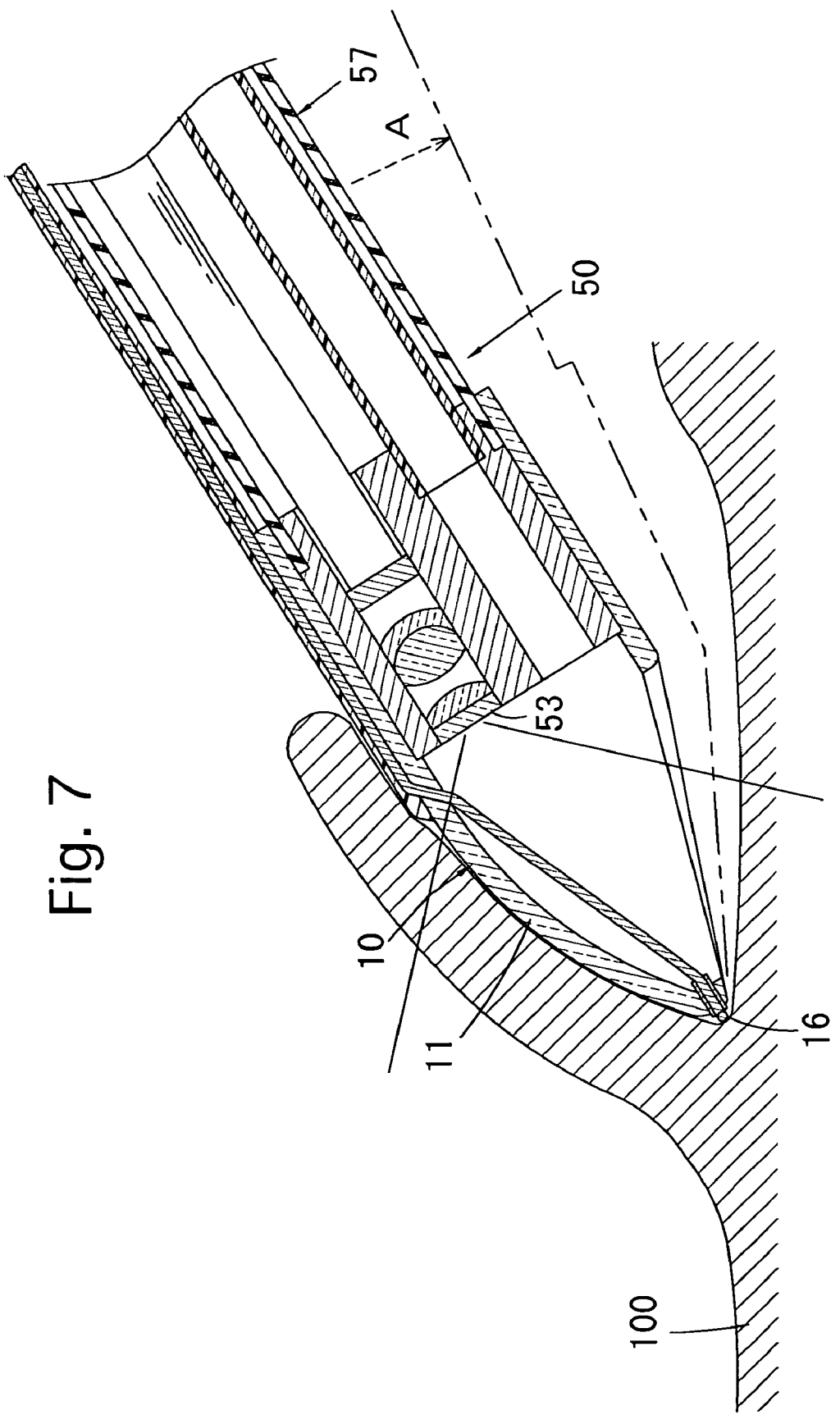
FIG. 7 is a cross sectional view of the first embodiment of the endoscopic high-frequency knife, showing an operational state thereof.

FIGS. 6 through 9 show different operational states of an endoscopic mucosal resection (EMR) with the use of the first embodiment of the endoscopic high-frequency knife 1. In the endoscopic mucosal resection, firstly saline or the like is injected into an affected area with an endoscopic needle-tipped injector 81, which is inserted into the treatment tool insertion channel 56 of the endoscope 50, to make the mucosa of the affected area swell as shown in FIG. 6. Subsequently, the high-frequency cutting electrode 16 is pressed against the mucosa and energized to thereby make it possible to dissect the submucosa as shown in FIG. 7.

In such a dissecting operation, the high-frequency cutting electrode 16 does not have to be steered to the affected area independently. Namely, the high-frequency cutting electrode 16 can be steered to a given affected area simply by steering the steerable bendable portion 57 of the endoscope 50. Moreover, one can perform this steering operation while viewing the conditions of the high-frequency cutting electrode 16 and the periphery thereof including dissected surfaces of the submucosa in real time through the transparent hood portion 11.

During such an operation, the cutting depth by the high-frequency cutting electrode 16 can be easily adjusted remotely by changing the direction of the tip of the insertion portion 58 of the endoscope 50 as shown by a dashed-line arrow A in FIG. 7 by manipulating the steerable bendable portion 57. In this manner a sinew between a mucosa and a lamina muscularis, which was formerly considered difficult to be cut, can be cut with precision to exfoliate the mucosa.

Figure 8:
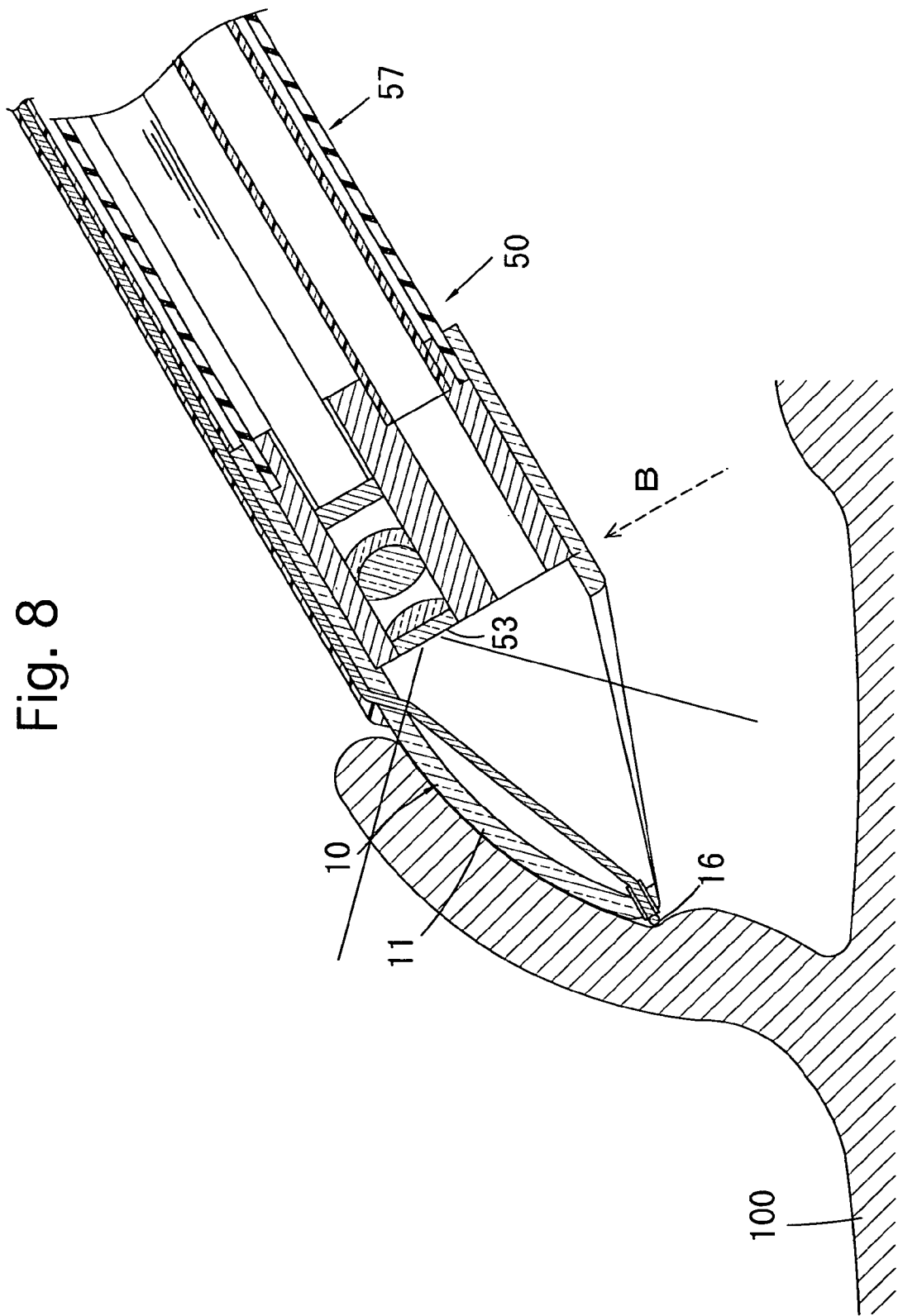
FIG. 8 is a cross sectional view of the first embodiment of the endoscopic high-frequency knife, showing an operational state thereof.
Figure 9:
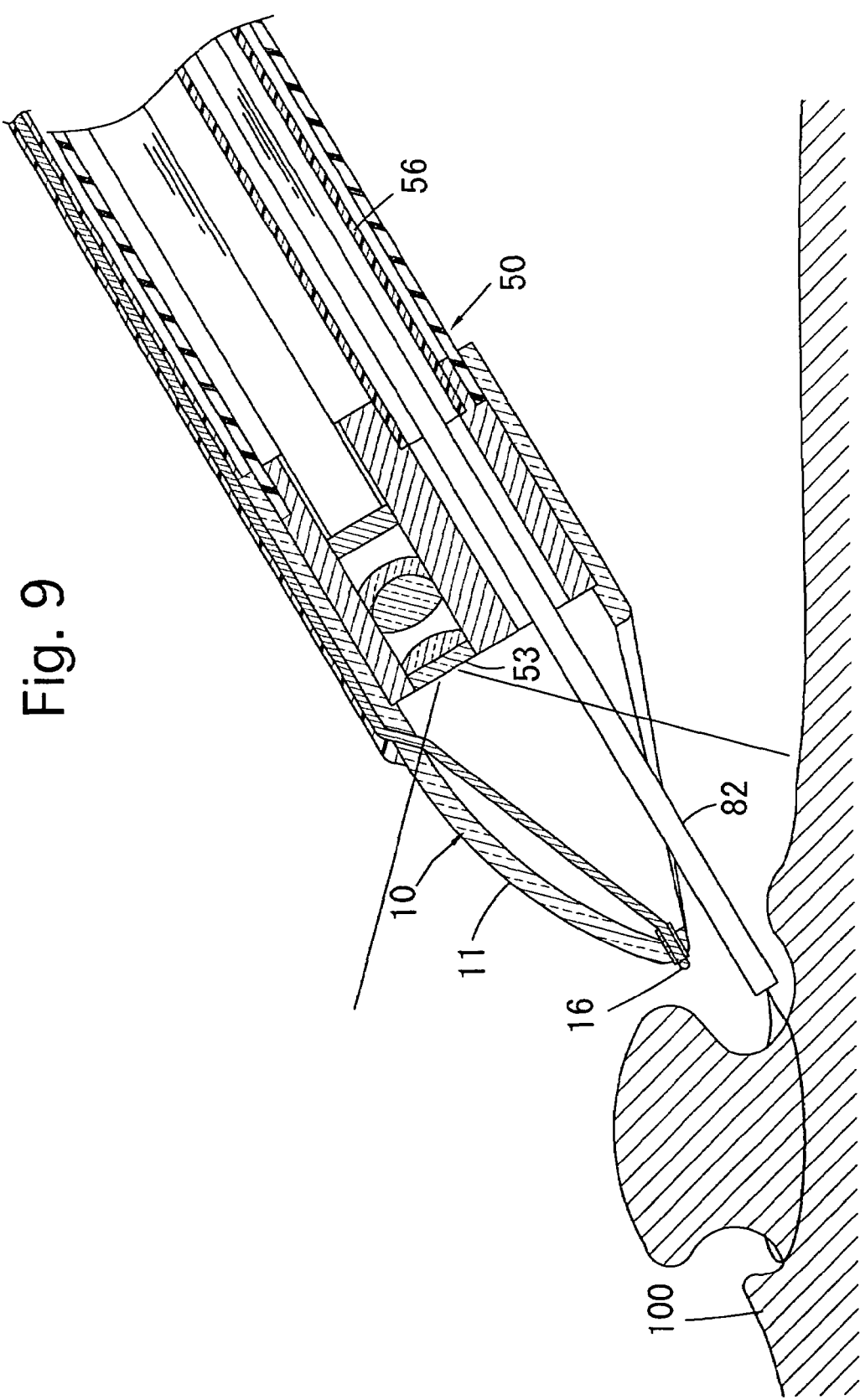
FIG. 9 is a cross sectional view of the first embodiment of the endoscopic high-frequency knife, showing an operational state thereof.

In addition, mucosa lying on the hood portion 11 can be lifted by remotely steering the steerable bendable portion 57 of the endoscope 50 as shown by a dashed-line arrow B in FIG. 8 to view the conditions of the dissected surfaces carefully, which makes it possible to easily determine the degree of dissection and also the necessity for an additional dissecting operation.

Thereafter, if necessary, various kinds of additional endoscopic operations to the body tissue 100 can be performed with the use of various endoscopic treatment tools such as an endoscopic high-frequency snare 82 (see FIG. 9) which is used by being introduced into the body through the treatment tool insertion channel 56 of the endoscope 50 to gain therapeutic effect.

[Second Embodiment]

Figure 10:
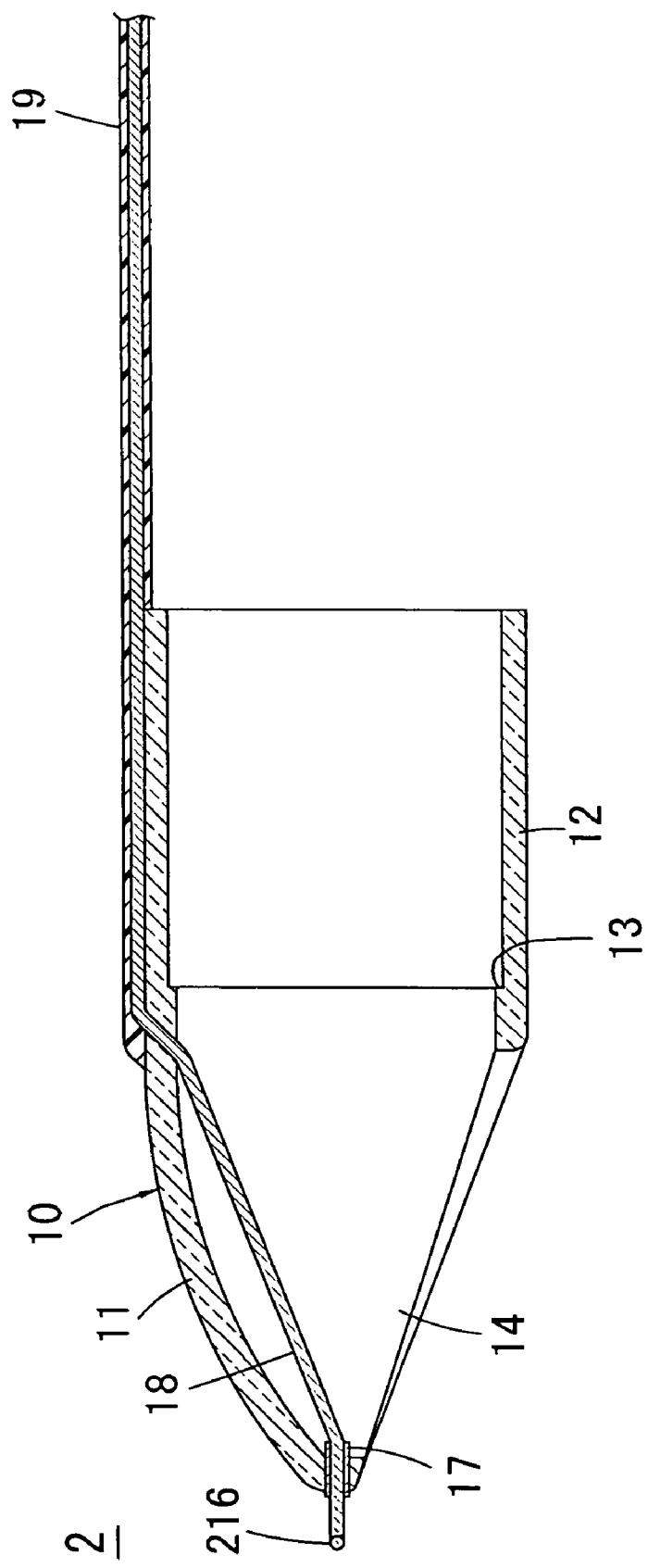
FIG. 10 is a cross sectional view of a second embodiment of the endoscopic high-frequency knife according to the present invention.
Figure 11:
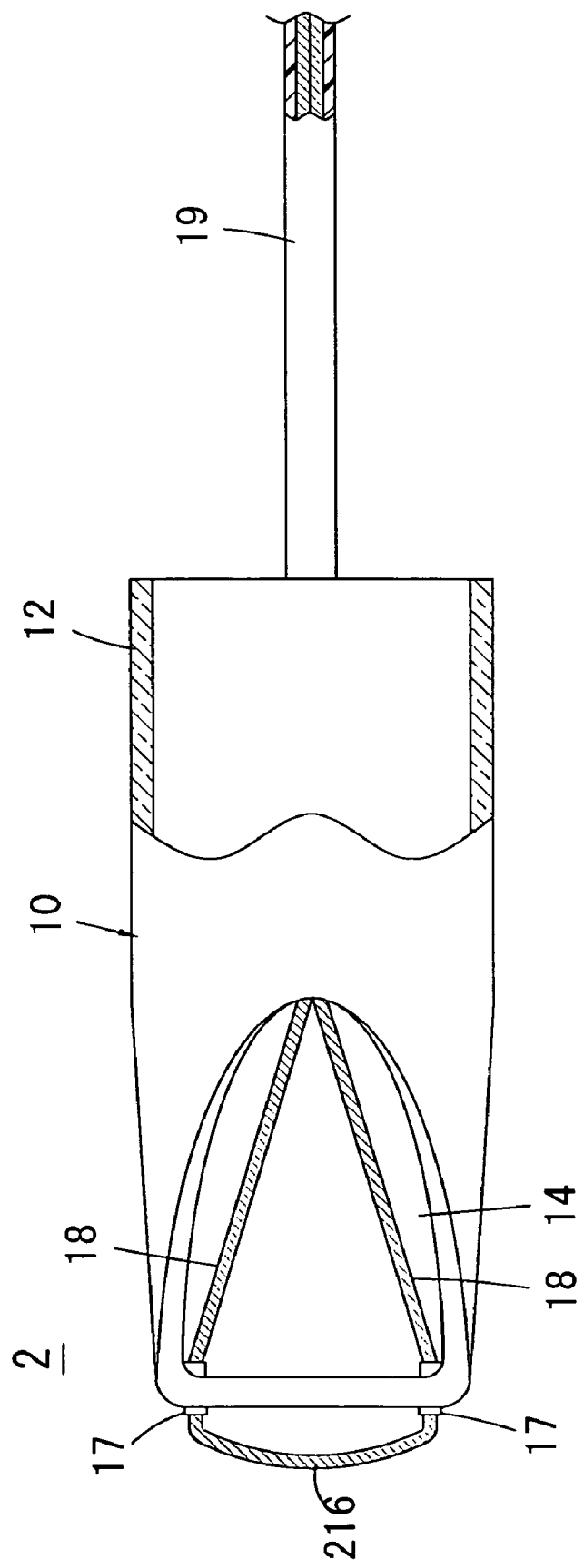
FIG. 11 is a bottom view of the second embodiment of the endoscopic high-frequency knife shown in FIG. 10.

FIG. 10 is a cross sectional view of a second embodiment of the endoscopic high-frequency knife 2 according to the present invention, while FIG. 11 is a bottom view thereof. In this embodiment, a high-frequency cutting electrode 216 is formed in an arc shape which bulges forward. In this manner, the shape of the high-frequency cutting electrode 216 is optional.

[Third Embodiment]

Figure 12:
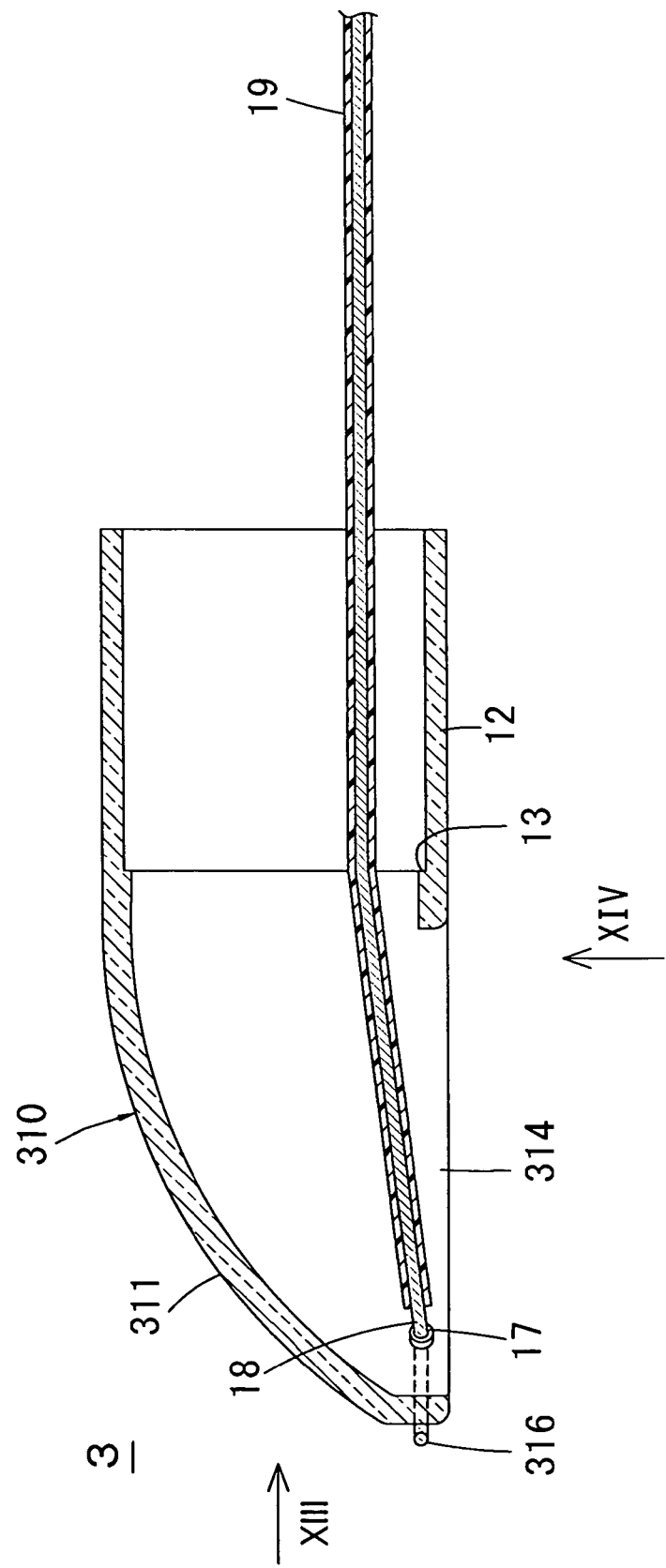
FIG. 12 is a cross sectional view of a third embodiment of the endoscopic high-frequency knife according to the present invention.
Figure 13:
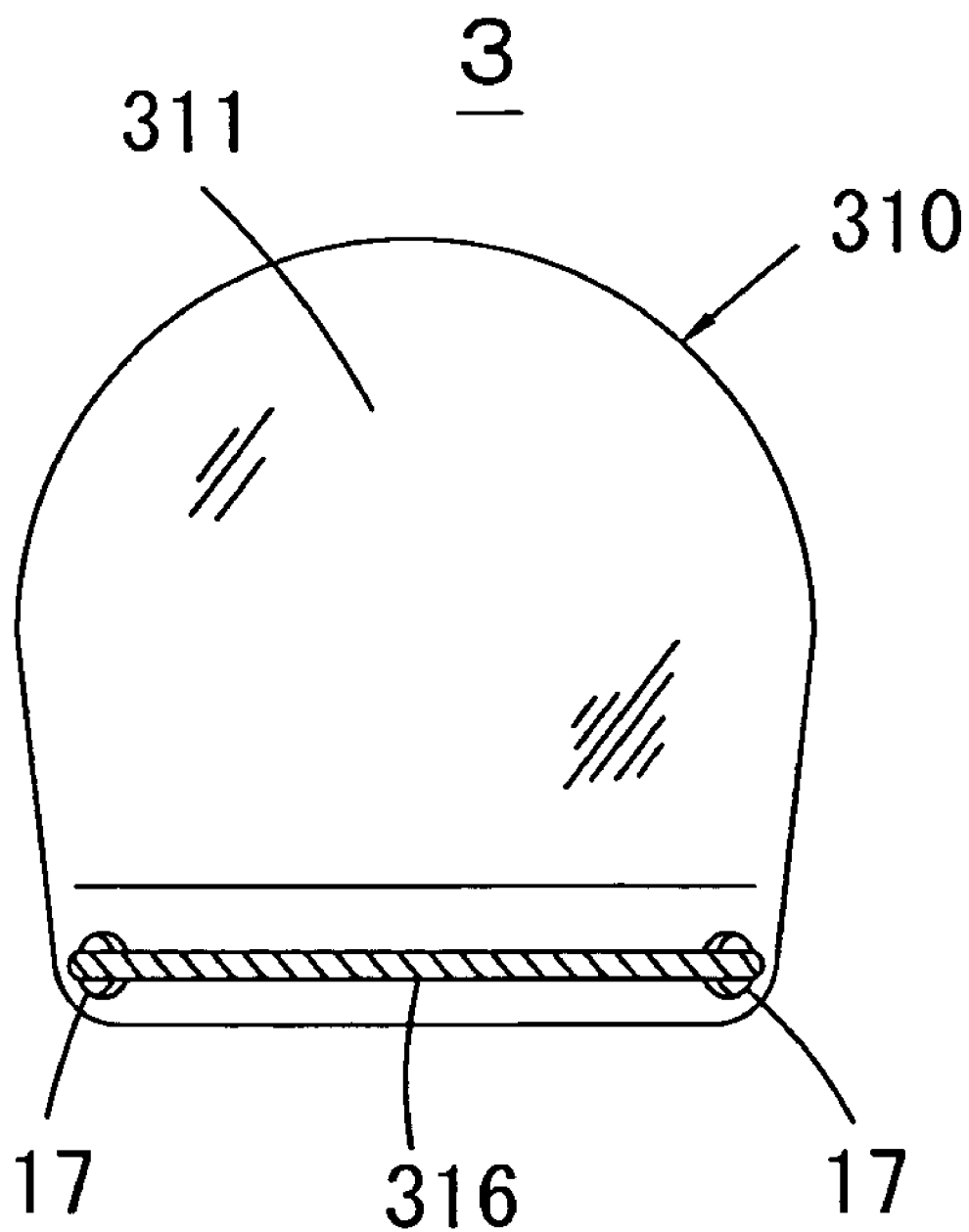
FIG. 13 is a front view of the third embodiment of the endoscopic high-frequency knife, viewed in the direction of an arrow XIII shown in FIG. 12.
Figure 14:
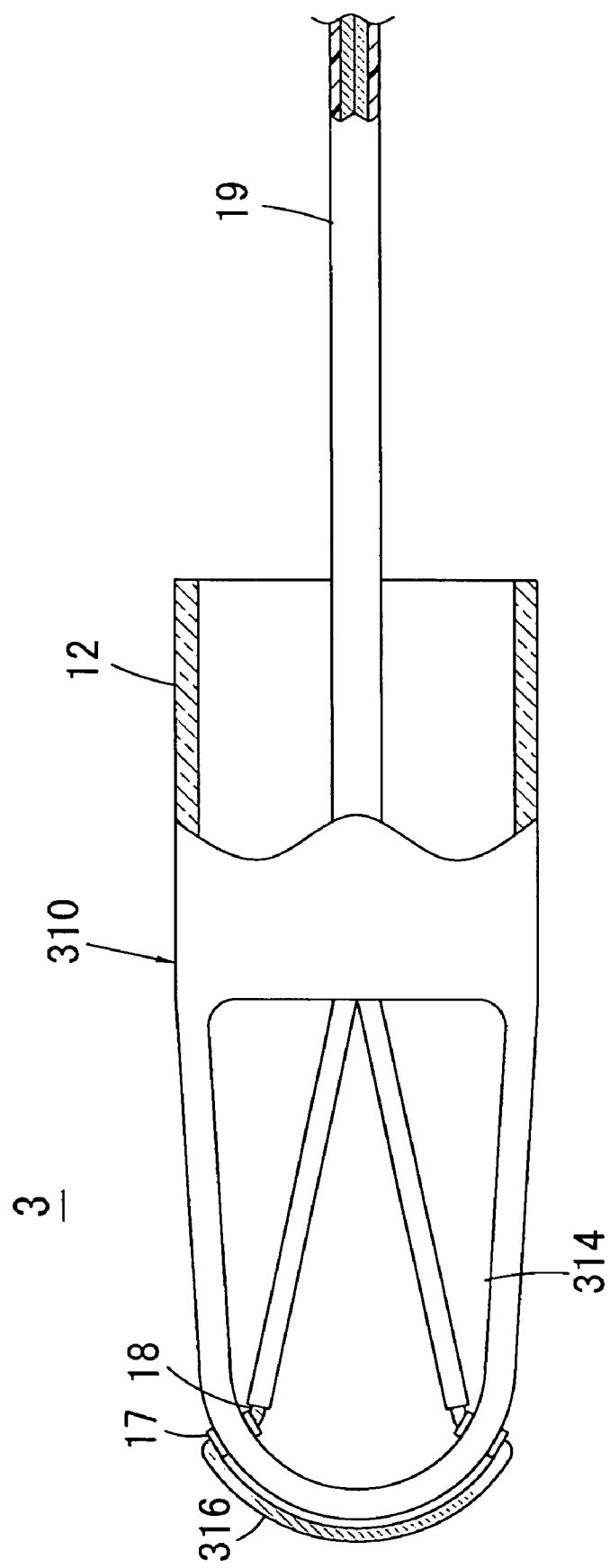
FIG. 14 is a bottom view, partly cross section, of the third embodiment of the endoscopic high-frequency knife, viewed in the direction of an arrow XIV shown in FIG. 12.

FIG. 12 is a cross sectional view of a third embodiment of the endoscopic high-frequency knife 3 according to the present invention, FIG. 13 is a front view thereof viewed in the direction of an arrow XIII shown in FIG. 12, and FIG. 14 is a bottom view, partly cross section, of the endoscopic high-frequency knife 3, viewed in the direction of an arrow XIV shown in FIG. 12. As shown in FIG. 14, the high-frequency cutting electrode 316 is formed in the shape of an arc which extends along the curved tip of a hood portion 311 of the transparent hood 310.

In the third embodiment of the endoscopic high-frequency knife 3, the hood portion 311 of the transparent hood 310 is shaped to fully cover the front of the distal end member 51 of the endoscope 50, the rear end of the opening 314 which is positioned in front of the end surface 52 being larger in a circumferential direction of the transparent hood 310, the two conductive wires 18 are drawn out directly from the rear end of the transparent hood 310 through the space inside the hood portion 311, and are inserted into the treatment tool insertion channel 56 when in use.

[Fourth Embodiment]

Figure 15:
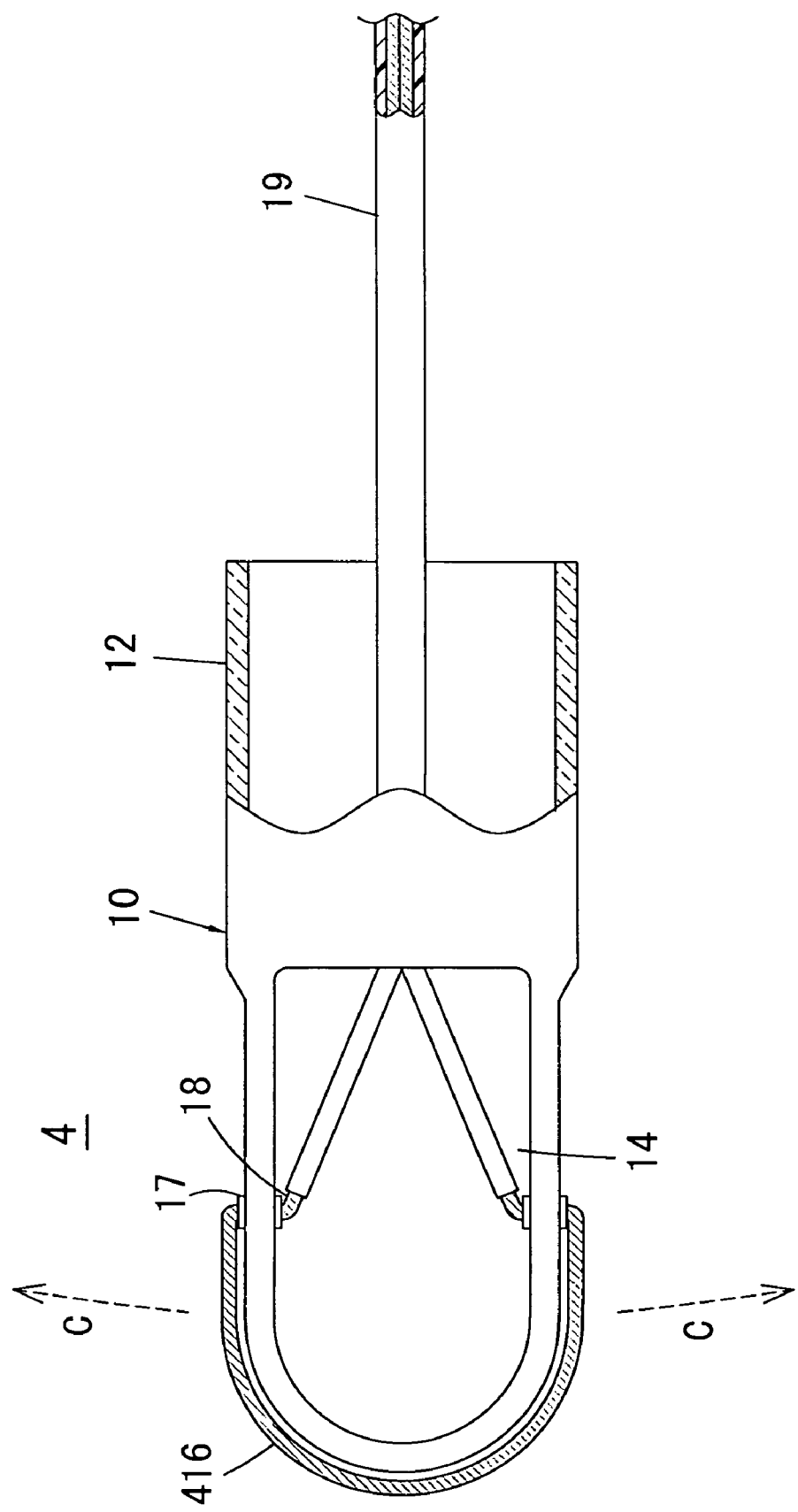
FIG. 15 is a bottom view of a fourth embodiment of the endoscopic high-frequency knife according to the present invention.

FIG. 15 is a bottom view of a fourth embodiment of the endoscopic high-frequency knife 4 according to the present invention. The fourth embodiment is substantially the same as the fourth embodiment of the endoscopic high-frequency knife 4 shown in FIGS. 12 through 14 except that the opposite ends of the high-frequency cutting electrode 416 are extended rearward to opposite side surfaces of the hood portion 11, respectively. This structure makes it possible for the endoscopic high-frequency knife 4 to dissect a mucosa positioned on the right-hand side or the left-hand side of the transparent hood 10 by moving the transparent hood 10 sideways as shown by dashed-line arrows C in FIG. 15.

It should be noted that the present invention is not limited solely to each of the above described first through fourth embodiments; for instance, the high-frequency cutting electrode 416 can be made of not only a conductive wire but also any other conductive member.

[Fifth Embodiment]

In an endoscopic high-frequency knife 5 of the fifth embodiment, the endoscope has an objective optical system positioned in the objective window.

Figure 16:
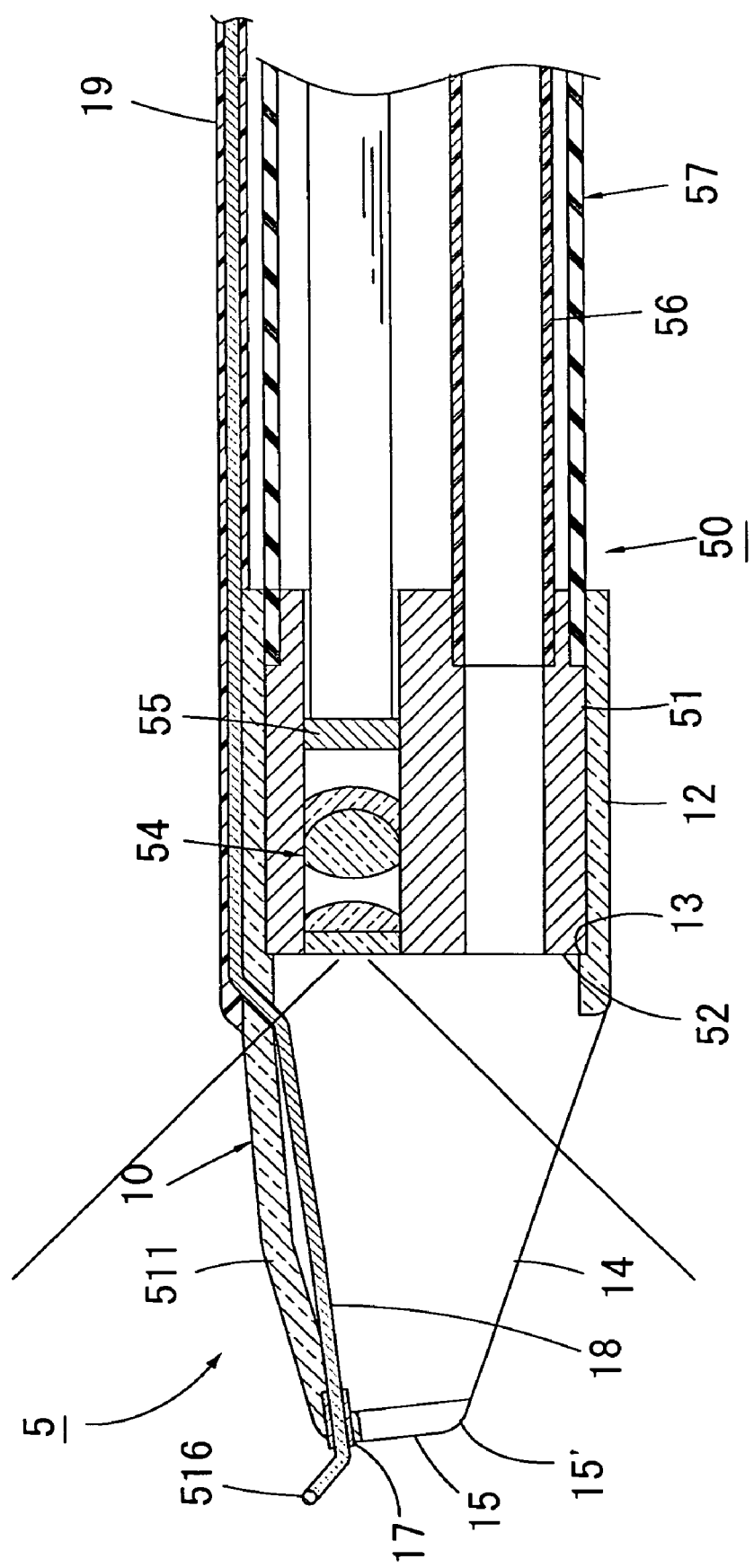
FIG. 16 is a cross sectional view of a fifth embodiment of the endoscopic high-frequency knife according to the present invention, and the distal end of an endoscope to which the endoscopic high-frequency knife is attached.
Figure 17:
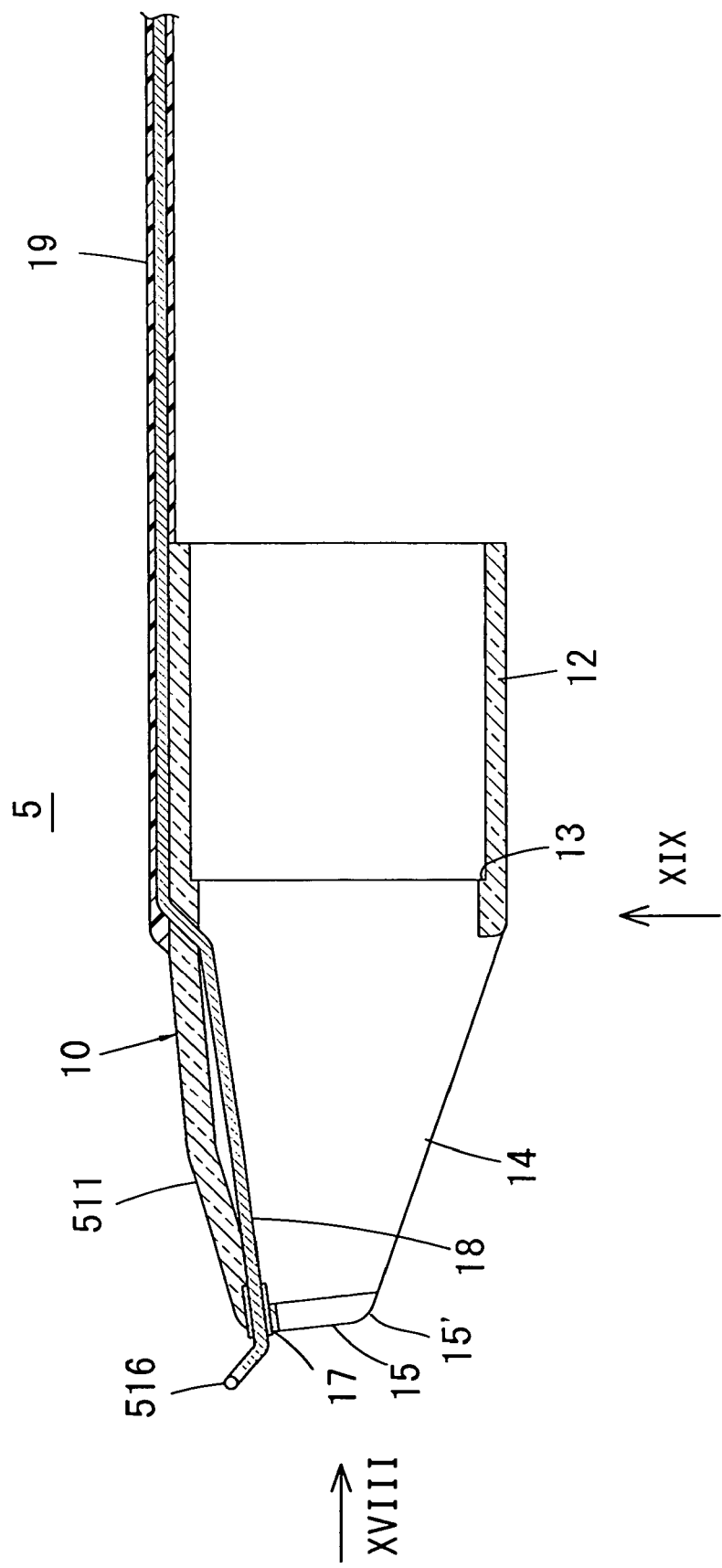
FIG. 17 is a cross sectional view of the fifth embodiment of the endoscopic high-frequency knife shown in FIG. 16.
Figure 18:
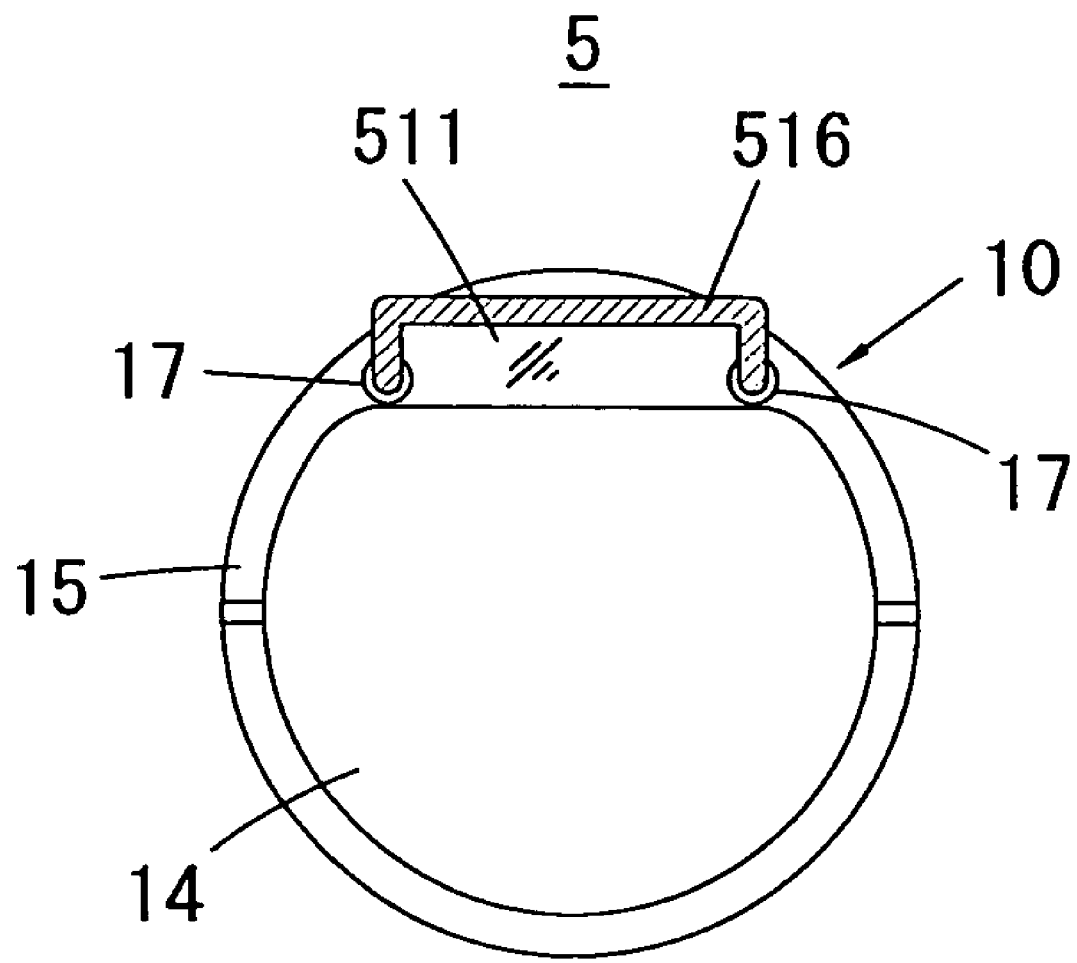
FIG. 18 is a front view of the fifth embodiment of the endoscopic high-frequency knife, viewed in the direction of an arrow XVIII shown in FIG. 17.
Figure 19:
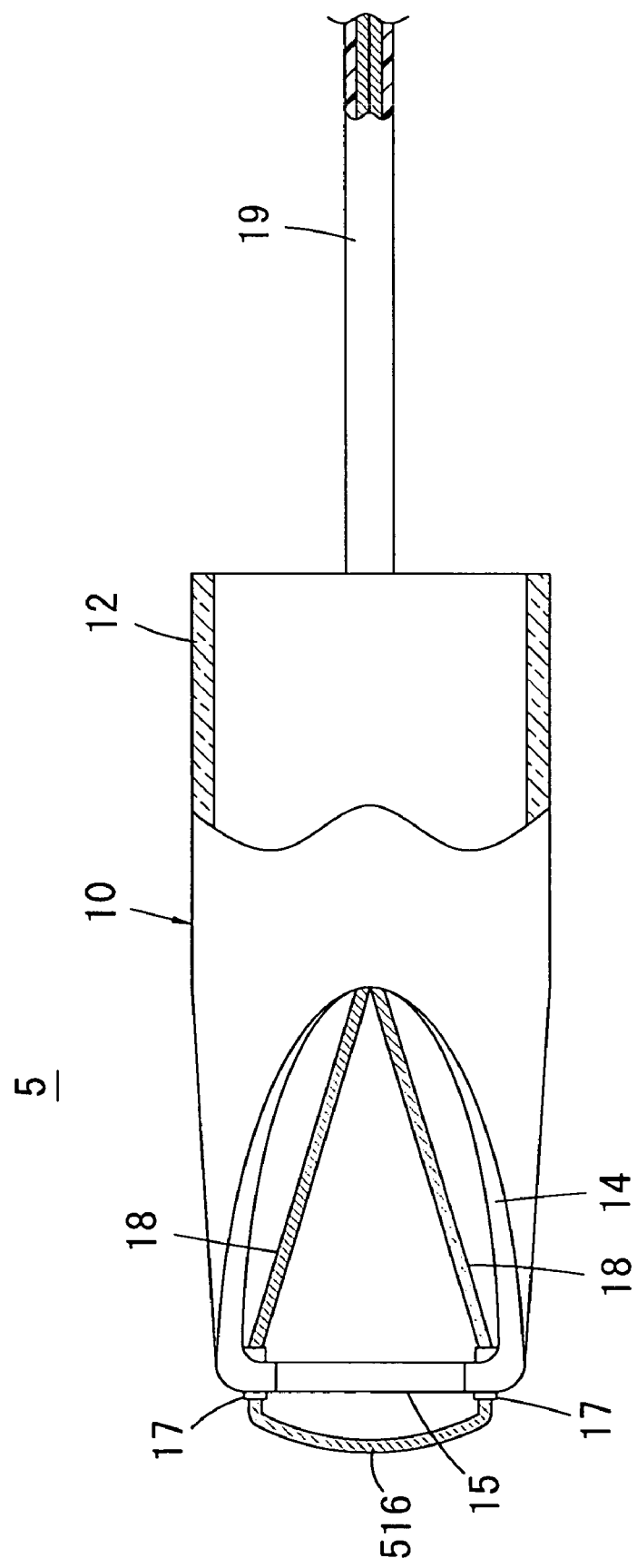
FIG. 19 is a bottom view, partly cross section, of the fifth embodiment of the endoscopic high-frequency knife, viewed in the direction of an arrow XIX shown in FIG. 17.

FIG. 16 is a cross sectional view of a fifth embodiment of the endoscopic high-frequency knife 5 according to the present invention, and the distal end of an endoscope 50, showing a state where the endoscopic high-frequency knife 5 is attached to the distal end of the endoscope 50. FIG. 17 is a cross sectional view of the endoscopic high-frequency knife 5, FIG. 18 is a front view of the endoscopic high-frequency knife 5, viewed in the direction of an arrow XVIII shown in FIG. 17, and FIG. 19 is a bottom view, partly cross section, of the endoscopic high-frequency knife 5, viewed in the direction of an arrow XIX shown in FIG. 17.

A rear half of the transparent hood 10 is formed as a mounting portion 12 having a cylindrical shape which can be removably fitted on an outer peripheral surface of the distal end member 51. The installation position of the transparent hood 10 on the distal end member 51 is determined by contact of the end surface 52 of the distal end member 51 with a stepped portion 13 that is formed on an inner peripheral surface of the mounting portion 12.

A front half of the transparent hood 10 is formed as a projecting portion 511 which firstly projects forward from a portion of the transparent hood 10 in the vicinity of the end surface 52 of the distal end member 51. It is sufficient enough for at least the projecting portion 511 of the transparent hood 10 to be optically transparent. In the fifth embodiment of the endoscopic high-frequency knife 5, the projecting portion 511 is formed as a hood shape, and a front end surface 15 of the transparent hood 10 has an opening which is communicatively connected to the opening 14.

A high-frequency cutting electrode 516 is attached to the tip of the transparent hood 10 which projects from the front end surface 15 so as to extend laterally by an upper edge of the front end surface 15 therealong. Accordingly, the conditions of the high-frequency cutting electrode 516 and its periphery can be viewed from the objective window 53 through the transparent projecting portion 511.

The high-frequency cutting electrode 516 is made of a conductive wire. The endoscopic high-frequency knife 5 is provided, at the tip of the projecting portion 511 in the vicinity of laterally-opposite ends thereof, with two heat-resistant pipes 17 made of ceramics, respectively, which are positioned laterally apart from each other and each of which penetrates through the tip of the projecting portion 511 in a forward/rearward direction of the transparent hood 10. The opposite ends of the high-frequency cutting electrode 516 are inserted into the two heat-resistant pipes 17 from the front ends thereof, respectively, so that the high-frequency cutting electrode 516 is attached to the tip of the projecting portion 511 to extend between the front ends of the two heat-resistant pipes 17. The high-frequency cutting electrode 516 is formed to slightly bulge forward as shown in FIG. 19; however, the high-frequency cutting electrode 516 can be formed straight.

Two conductive wires 18 which extend from the opposite ends of the high-frequency cutting electrode 516 come out from the rear ends of the two heat-resistant pipes 17, respectively, to be drawn out from the transparent hood 10 in the vicinity of the mounting portion 12 through the space inside the projecting portion 511, and are subsequently extended rearward as a conductive cable (two-wire cable) 19.

Figure 20:
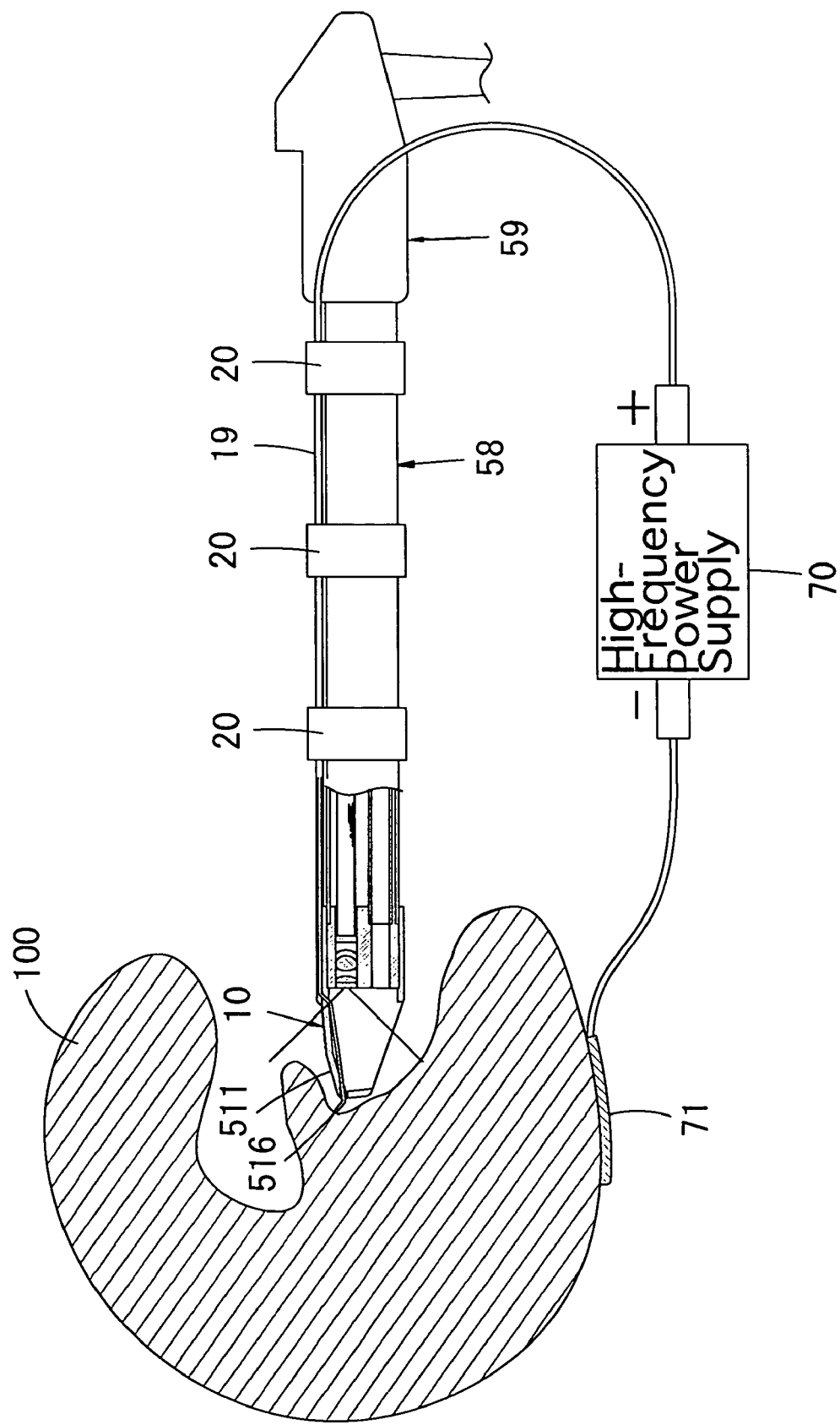
FIG. 20 is a schematic diagram showing a state where the fifth embodiment of the endoscopic high-frequency knife is set to dissect a submucosa of a body tissue with the endoscopic high-frequency knife.

FIG. 20 shows a state where the fifth embodiment of the endoscopic high-frequency knife 5 is set to dissect a submucosa of a body tissue 100 therewith. In this state, the conductive cable 19 which is drawn from the transparent hood 10 to extend rearward is fixed on an insertion portion 58 of the endoscope 50 along a lengthwise direction thereof by fixing bands 20, so that the rear end of the conductive cable 19 is connected to a positive terminal of a high-frequency power supply 70. A counter electrode 71 which is in contact with a large area of an outer surface of the body tissue 100 is connected to a negative terminal of the high-frequency power supply 70. The reference numeral 59 shown in FIG. 20 designates an operational portion of the endoscope 50.

Figure 21:
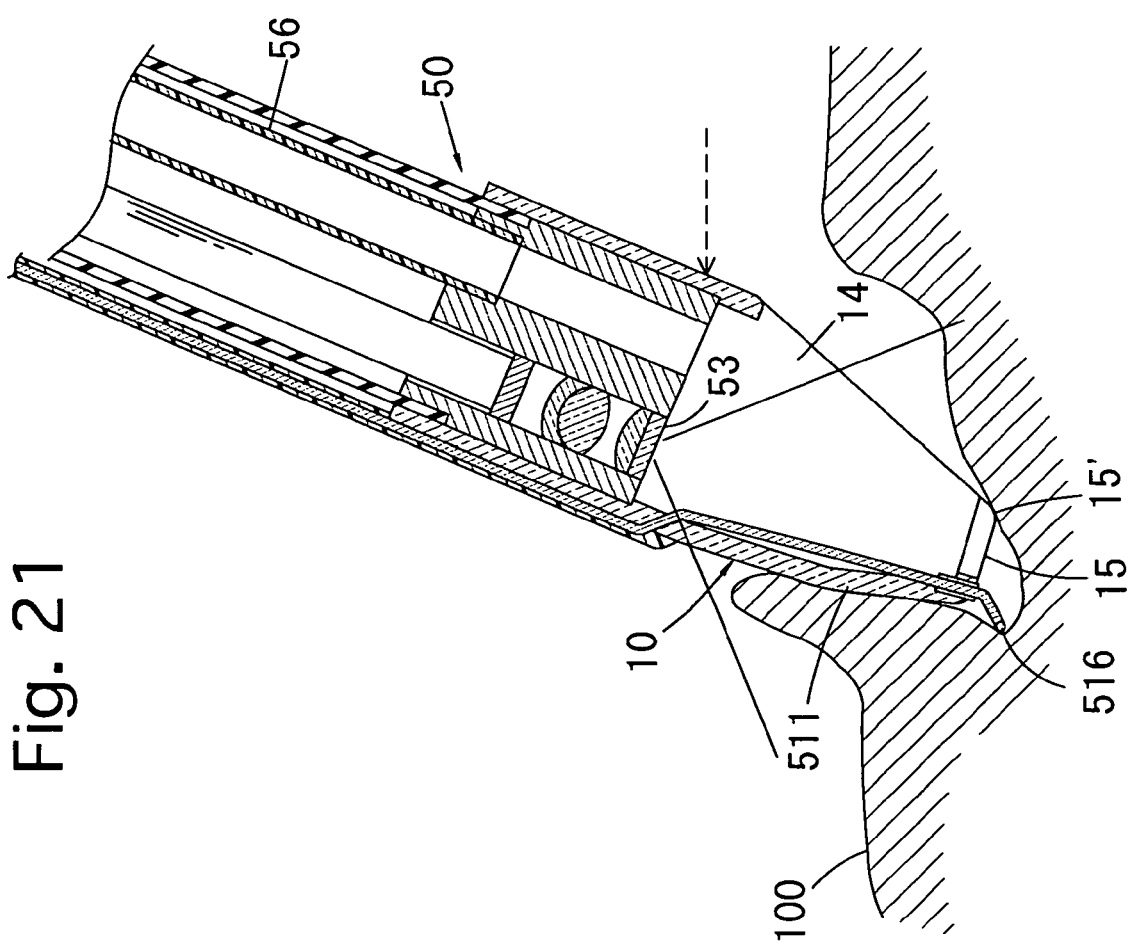
FIG. 21 is a cross sectional view of the fifth embodiment of the endoscopic high-frequency knife, showing an operational state thereof.

FIG. 21 shows an operational state of an endoscopic mucosal resection (EMR) with the use of the fifth embodiment of the endoscopic high-frequency knife 5. In the endoscopic mucosal resection, the high-frequency cutting electrode 516 is pressed against a mucosa of the body tissue 100 and energized to thereby make it possible to dissect the submucosa as shown in FIG. 21.

In such a dissecting operation, the high-frequency cutting electrode 516 does not have to be steered to the affected area independently. Namely, the high-frequency cutting electrode 516 can be steered to a given affected area simply by steering the steerable bendable portion 57 of the endoscope 50. Moreover, one can perform this steering operation while viewing the conditions of the high-frequency cutting electrode 516 and its periphery including dissected surfaces of the submucosa in real time through the transparent projecting portion 511.

During such an operation, the cutting depth by the high-frequency cutting electrode 516 can be easily adjusted remotely by changing the direction of the tip of the insertion portion 58 of the endoscope 50 by manipulating the steerable bendable portion 57. At the same time, a lower end point 15' of the front end surface 15 of the transparent hood 10 can serve as a fulcrum. In this manner a sinew between a mucosa and a lamina muscularis which was formerly considered difficult to be cut can be cut with precision to exfoliate the mucosa.

In the fifth embodiment of the endoscopic high-frequency knife 5, since the opening 14 and the front end surface 15 are open to be communicatively connected to each other, a treatment tool and the like which is inserted into the treatment tool insertion channel 56 from its insertion opening (not shown) can be made to project outwards from the projecting portion 511, so that various endoscopic operations other than the endoscopic surgical operation using the endoscopic high-frequency knife 5 can be performed before and after the endoscopic surgical operation using the endoscopic high-frequency knife 5.

[Sixth Embodiment]

Figure 22:
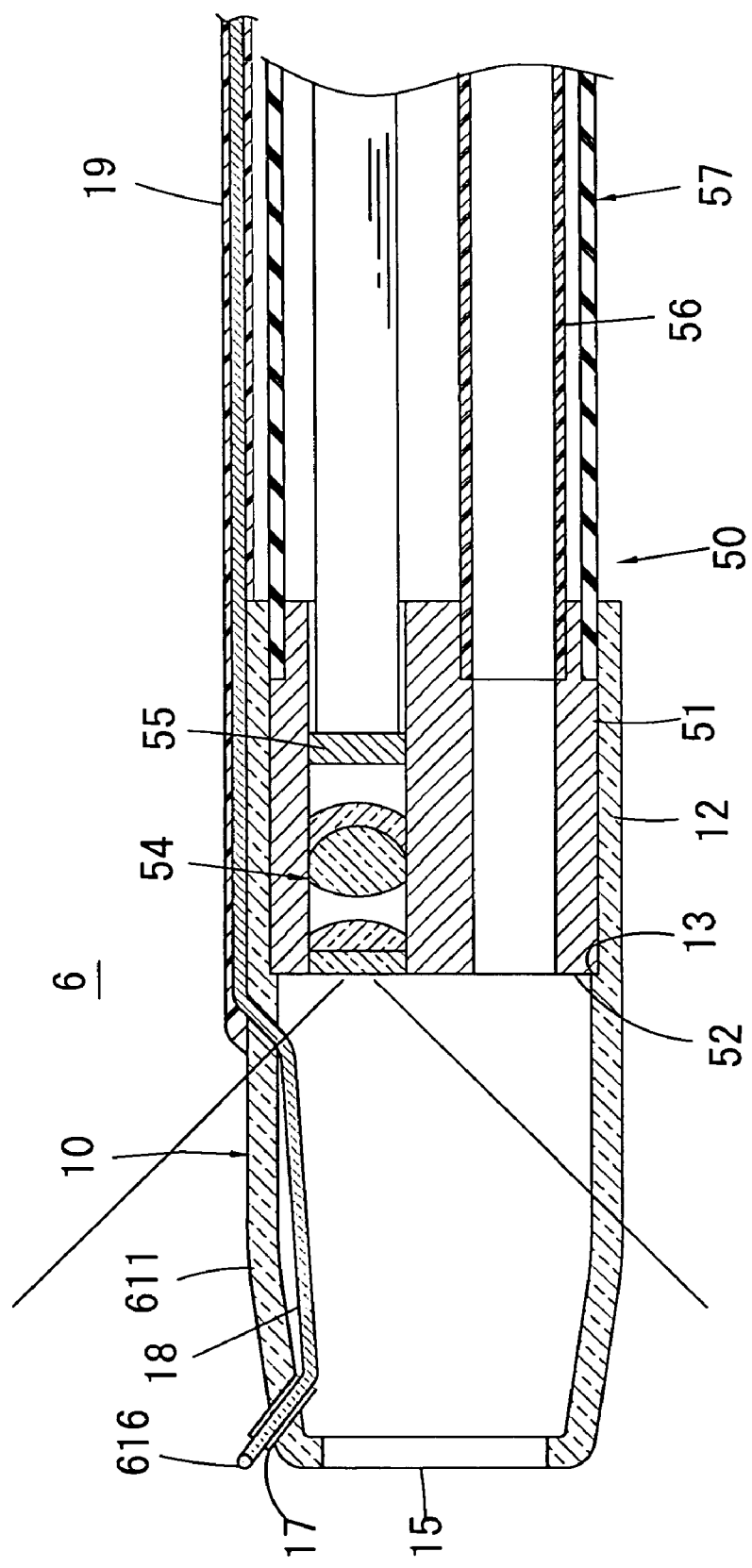
FIG. 22 is a cross sectional view of a sixth embodiment of the endoscopic high-frequency knife according to the present invention, and the distal end of an endoscope to which the endoscopic high-frequency knife is attached.

FIG. 22 shows a sixth embodiment of the endoscopic high-frequency knife 6 according to the present invention. In the sixth embodiment, a projecting portion 611 of the transparent hood 10 which corresponds to the projecting portion 111 shown in FIGS. 16 through 18 is formed in a substantially cylindrical shape, while the high-frequency cutting electrode 616 that extends laterally across an upper edge of the front end surface 15 therealong is positioned in the vicinity of the tip of the projecting portion 611. This embodiment also makes it possible for one to steer the high-frequency cutting electrode 616 to a given affected area simply by steering the steerable bendable portion 57 of the endoscope 50. Moreover, one can perform this steering operation while viewing the conditions of the high-frequency cutting electrode 616 and its periphery including dissected surfaces of the submucosa in real time through the transparent projecting portion 611, similar to the steering operation using the fifth embodiment of the endoscopic high-frequency knife.

[Seventh Embodiment]

In an endoscopic high-frequency knife 7 of the seventh embodiment, a transparent cylindrical projecting portion 711 is formed on the transparent hood 10 to project forward from a portion of the hood in a vicinity of a whole outer edge of the end surface, and a high-frequency cutting electrode 716 attached to a tip of the hood to project forward from a front end surface of the transparent cylindrical projecting portion so as to extend across a tip of the transparent cylindrical projecting portion.

Figure 23:
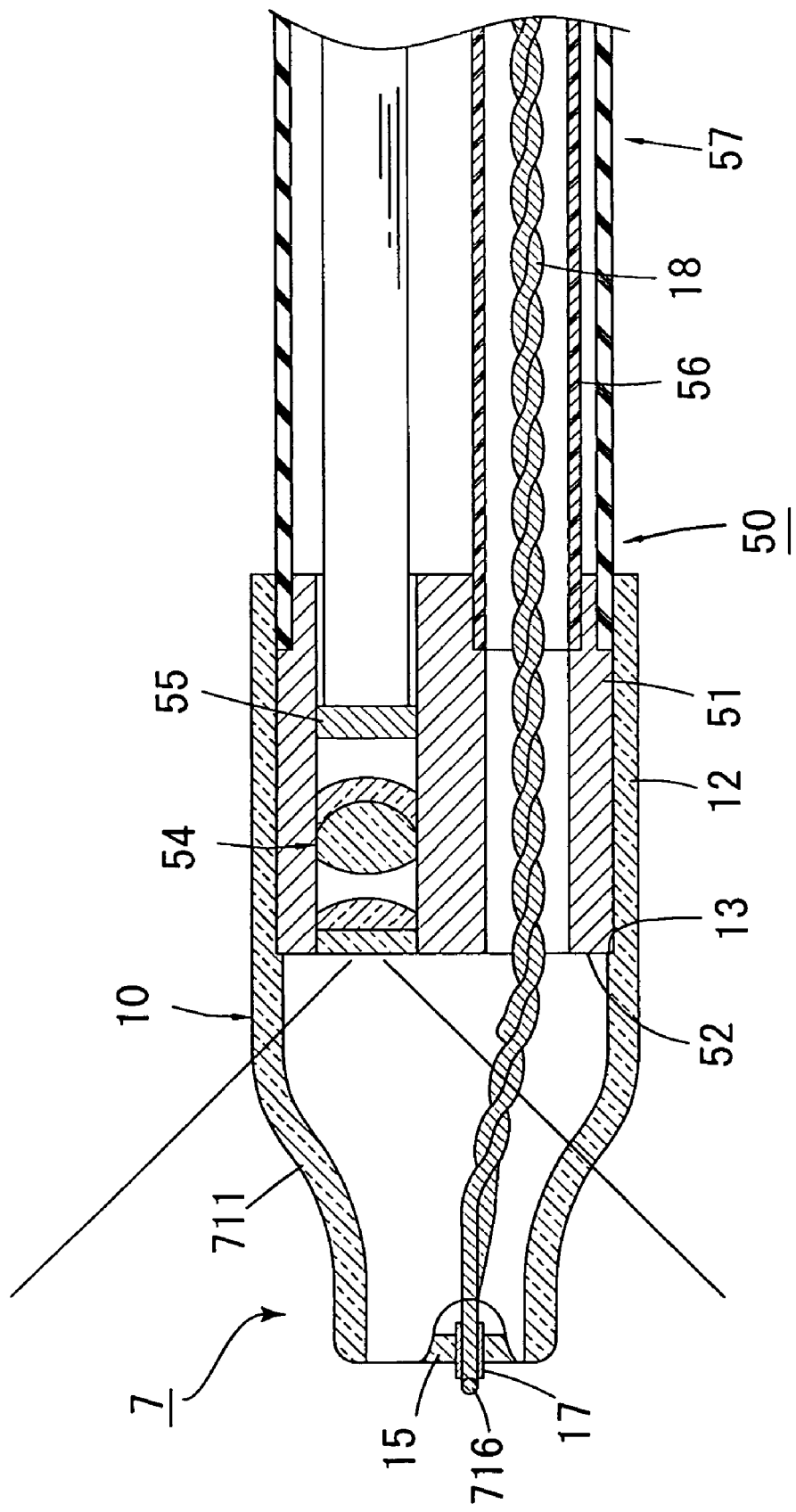
FIG. 23 is a cross sectional view of a seventh embodiment of the endoscopic high-frequency knife according to the present invention, and. the distal end of an endoscope to which the endoscopic high-frequency knife is attached.
Figure 24:
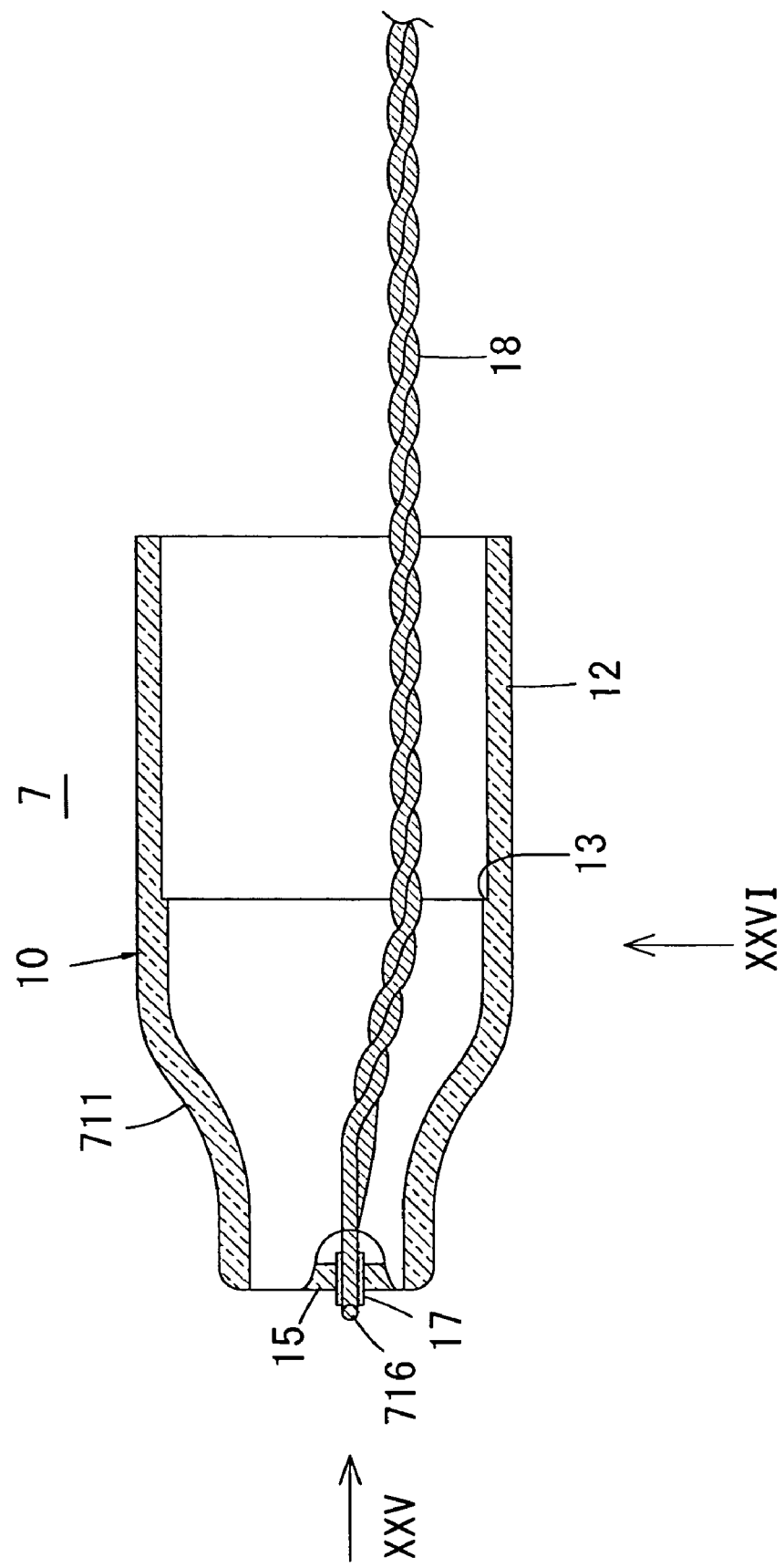
FIG. 24 is a cross sectional view of the seventh embodiment of the endoscopic high-frequency knife shown in FIG. 23.
Figure 25:
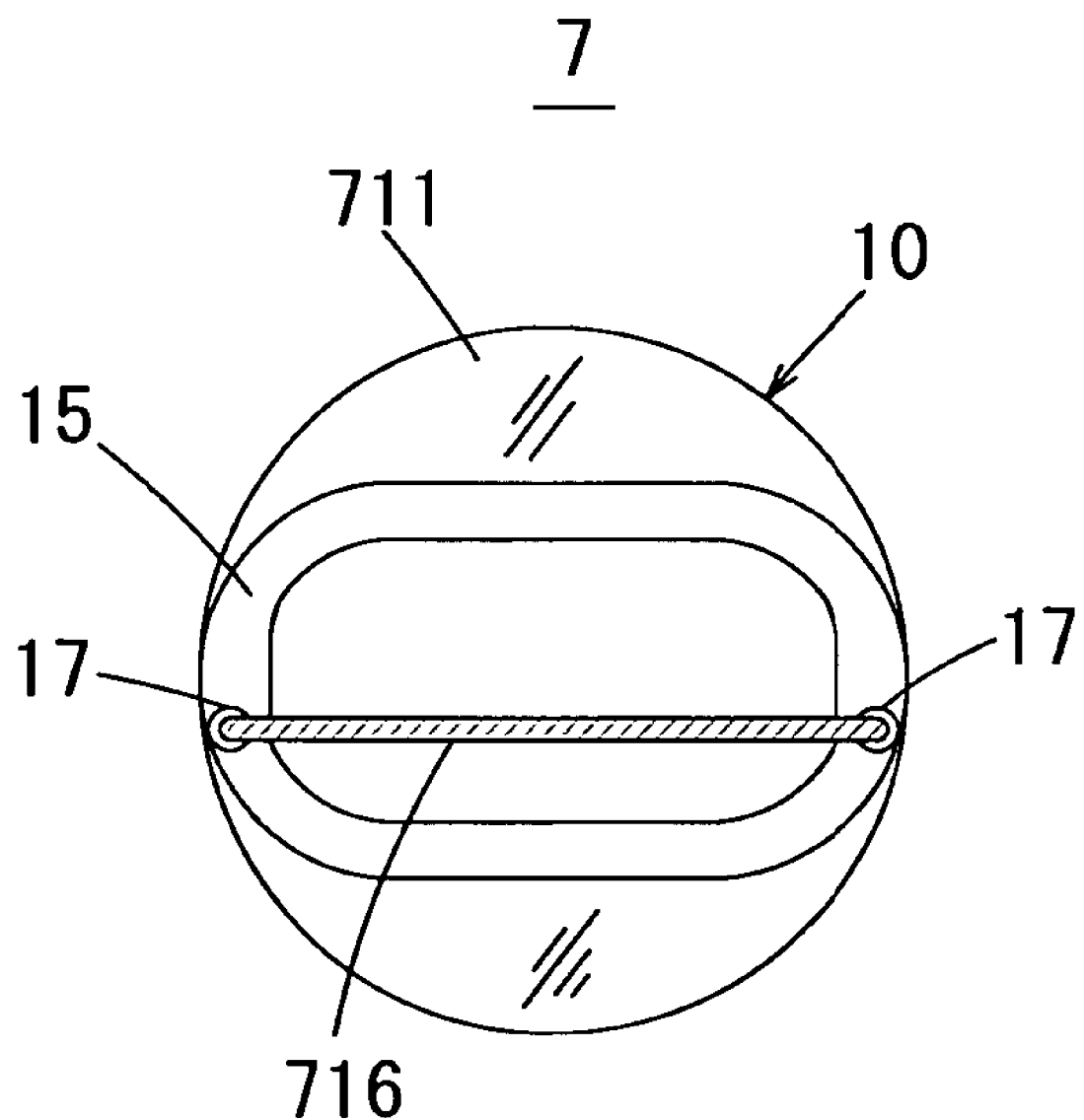
FIG. 25 is a front view of the seventh embodiment of the endoscopic high-frequency knife, viewed in the direction of an arrow XXV shown in FIG. 24.
Figure 26:
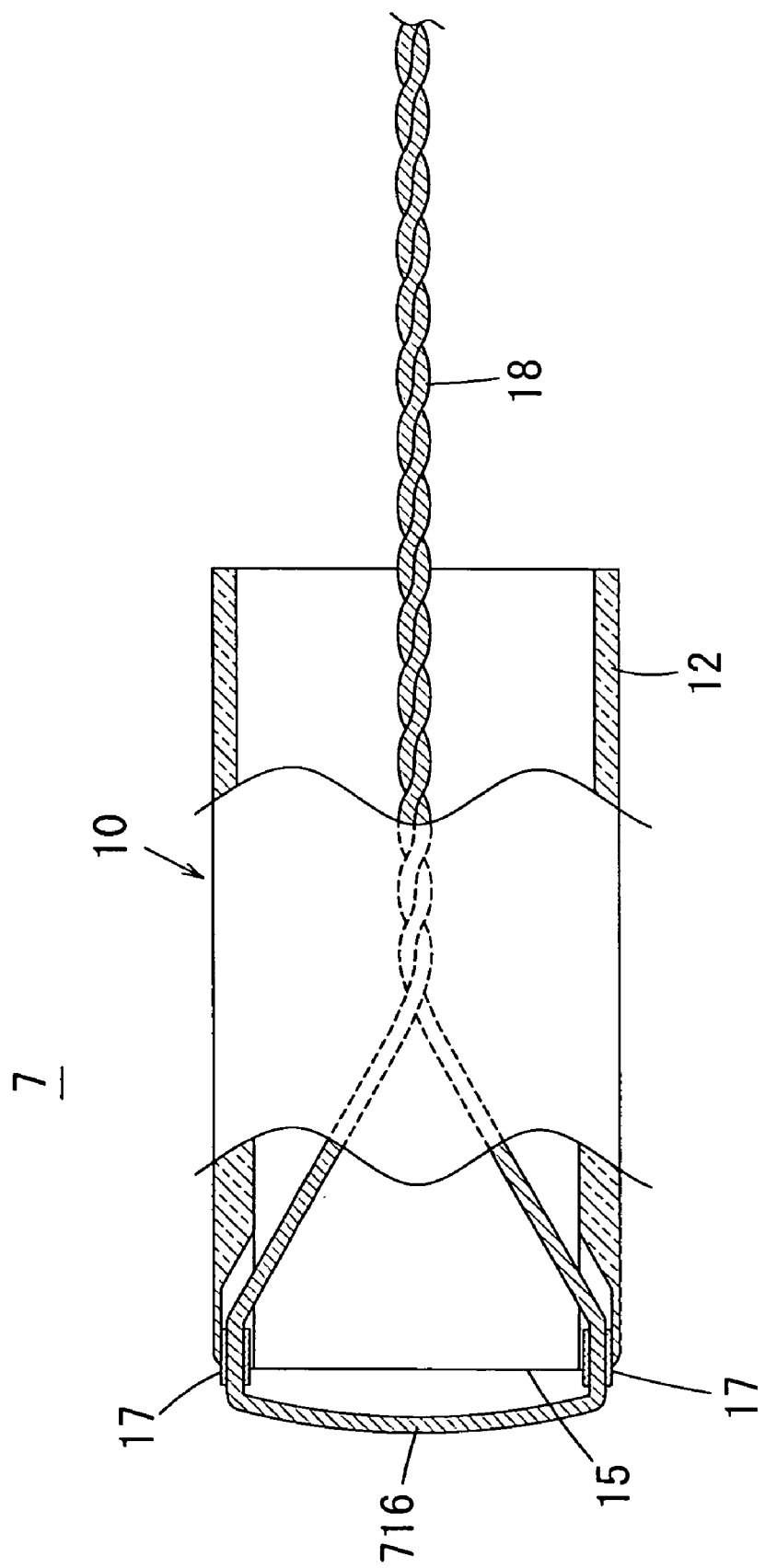
FIG. 26 is a bottom view, partly cross section, of the seventh embodiment of the endoscopic high-frequency knife, viewed in the direction of an arrow XXVI shown in FIG. 24.

FIG. 23 is a cross sectional view of a seventh embodiment of the endoscopic high-frequency knife 7 according to the present invention, and the distal end of an endoscope 50, showing a state where the endoscopic high-frequency knife 7 is attached to the distal end of the endoscope 50. FIG. 24 is a cross sectional view of the endoscopic high-frequency knife 7, FIG. 25 is a front view of the endoscopic high-frequency knife 7, viewed in the direction of an arrow XXV shown in FIG. 24, and FIG. 26 is a bottom view, partly cross section, of the endoscopic high-frequency knife 7, viewed in the direction of an arrow XXVI shown in FIG. 24.

A rear half of the transparent hood 10 is formed as a mounting portion 12 having a cylindrical shape which can be removably fitted on an outer peripheral surface of the distal end member 51. The installation position of the transparent hood 10 on the distal end member 51 is determined by contact of the end surface 52 of the distal end member 51 with a stepped portion 13 that is formed on an inner peripheral surface of the mounting portion 12.

The transparent cylindrical projecting portion 711 which projects forward from a portion of said transparent hood 10 in the vicinity of the whole outer edge of the end surface 52 of the distal end member 51. The transparent hood 10 will do if at least the cylindrical projecting portion 711 is optically transparent. A front end portion of the cylindrical projecting portion 711 is formed to be narrower vertically (in a vertical direction as viewed in FIG. 25) than the remaining portion of the cylindrical projecting portion 711. The front end surface 15 of the cylindrical projecting portion 711 has a substantially horizontally-elongated rectangular shape as shown in FIG. 25, but can be a horizontally-elongated elliptical shape.

A high-frequency cutting electrode 716 is attached to the tip of the transparent hood 10 to project forward from the front end surface 15 of the cylindrical projecting portion 711 so as to extend across the tip of the cylindrical projecting portion 711 in a direction of the major axis of the front end surface 15. Accordingly, the conditions of the high-frequency cutting electrode 716 and the periphery thereof can be viewed from the objective window 53 through the transparent cylindrical projecting portion 711. It is desirable that the depth of field of the objective optical system 54 be determined to be suitable for such structure of the endoscopic high-frequency knife 7. The usability of the endoscopic high-frequency knife 7 becomes greatest if the distance from the objective window 53 to the high-frequency cutting electrode 716 is about a little over 10 mm.

The high-frequency cutting electrode 716 is made of a conductive wire. The endoscopic high-frequency knife 7 is provided, at the tip of the cylindrical projecting portion 711 in the vicinity of laterally-opposite ends thereof, with two heat-resistant pipes 17 made of ceramics, respectively, which are positioned laterally apart from each other and each of which penetrates through the tip of the cylindrical projecting portion 711 in a forward/rearward direction of the transparent hood 10. The opposite ends of the high-frequency cutting electrode 716 are inserted into the two heat-resistant pipes 17 from the front ends thereof, respectively, so that the high-frequency cutting electrode 716 is attached to the tip of the cylindrical projecting portion 711 to extend between the front ends of the two heat-resistant pipes 17. The high-frequency cutting electrode 716 is formed to slightly bulge forward as shown in FIG. 26. However, the high-frequency cutting electrode 716 can be formed straight.

Two conductive wires 18 which extend from the opposite ends of the high-frequency cutting electrode 716 come out from the rear ends of the two heat-resistant pipes 17, respectively, to be drawn out rearward from the transparent hood 10 in the vicinity of the mounting portion 12 through the space inside the cylindrical projecting portion 711. When the endoscopic high-frequency knife 7 is used, the two conductive wires 18 which are twisted to serve as a twisted pair of conductive wires as shown in FIGS. 23, 24 and 26 are drawn through the treatment tool insertion channel 56 to be positioned therein.

Figure 27:
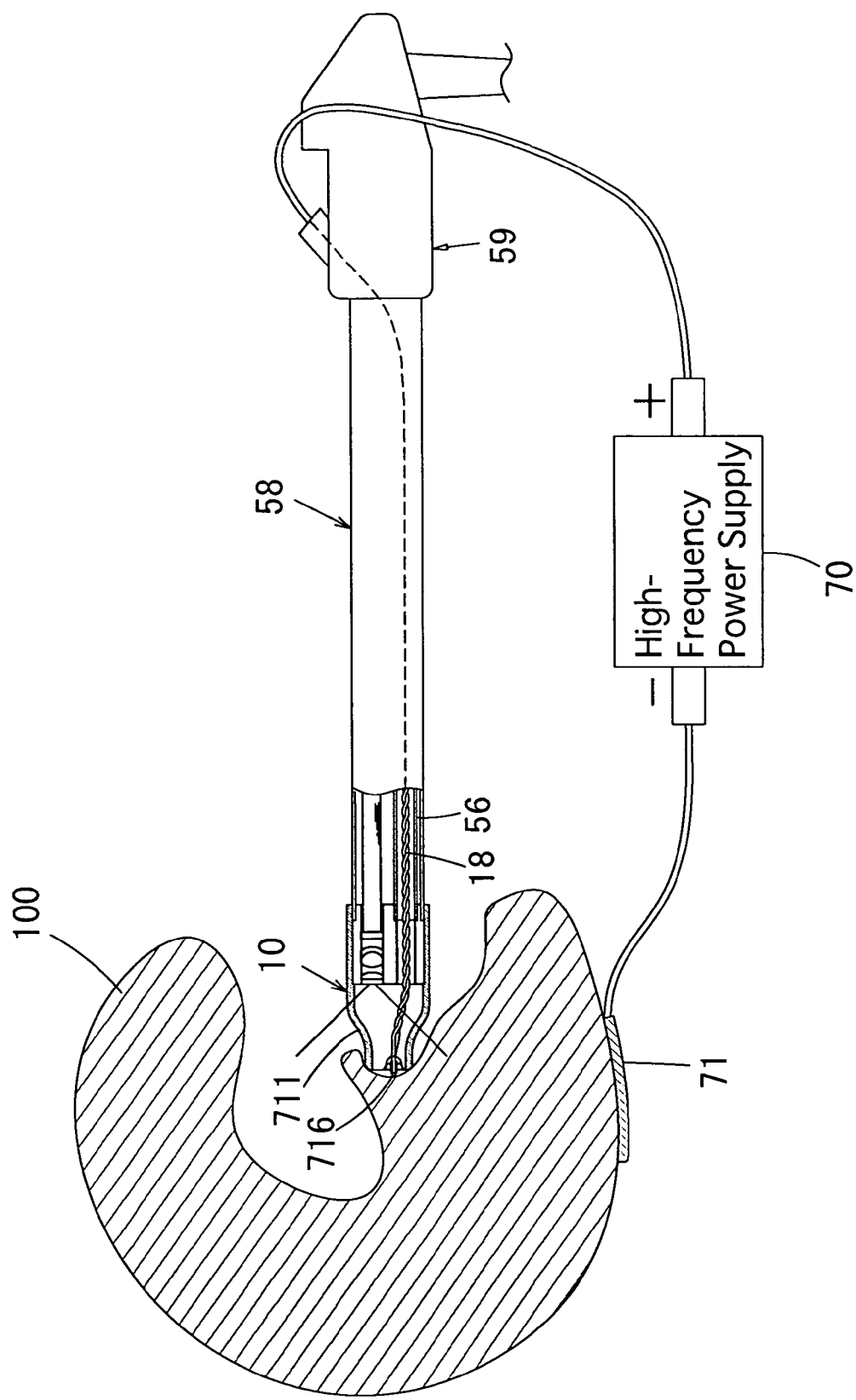
FIG. 27 is a schematic diagram showing a state where the seventh embodiment of the endoscopic high-frequency knife is set to dissect a submucosa of a body tissue with the endoscopic high-frequency knife.

FIG. 27 shows a state where the seventh embodiment of the endoscopic high-frequency knife 7 is set to dissect a submucosa of a body tissue 100. In this state, the twisted pair of conductive wires 18, which are drawn from the transparent hood 10 to extend rearward, passes through the treatment tool insertion channel 56 to be connected to a positive terminal of a high-frequency power supply 70. A counter electrode 71 which is in contact with a large area of an outer surface of the body tissue 100 is connected to a negative terminal of the high-frequency power supply 70. The reference numeral 59 shown in FIG. 27 designates an operational portion of the endoscope 50.

Figure 28:
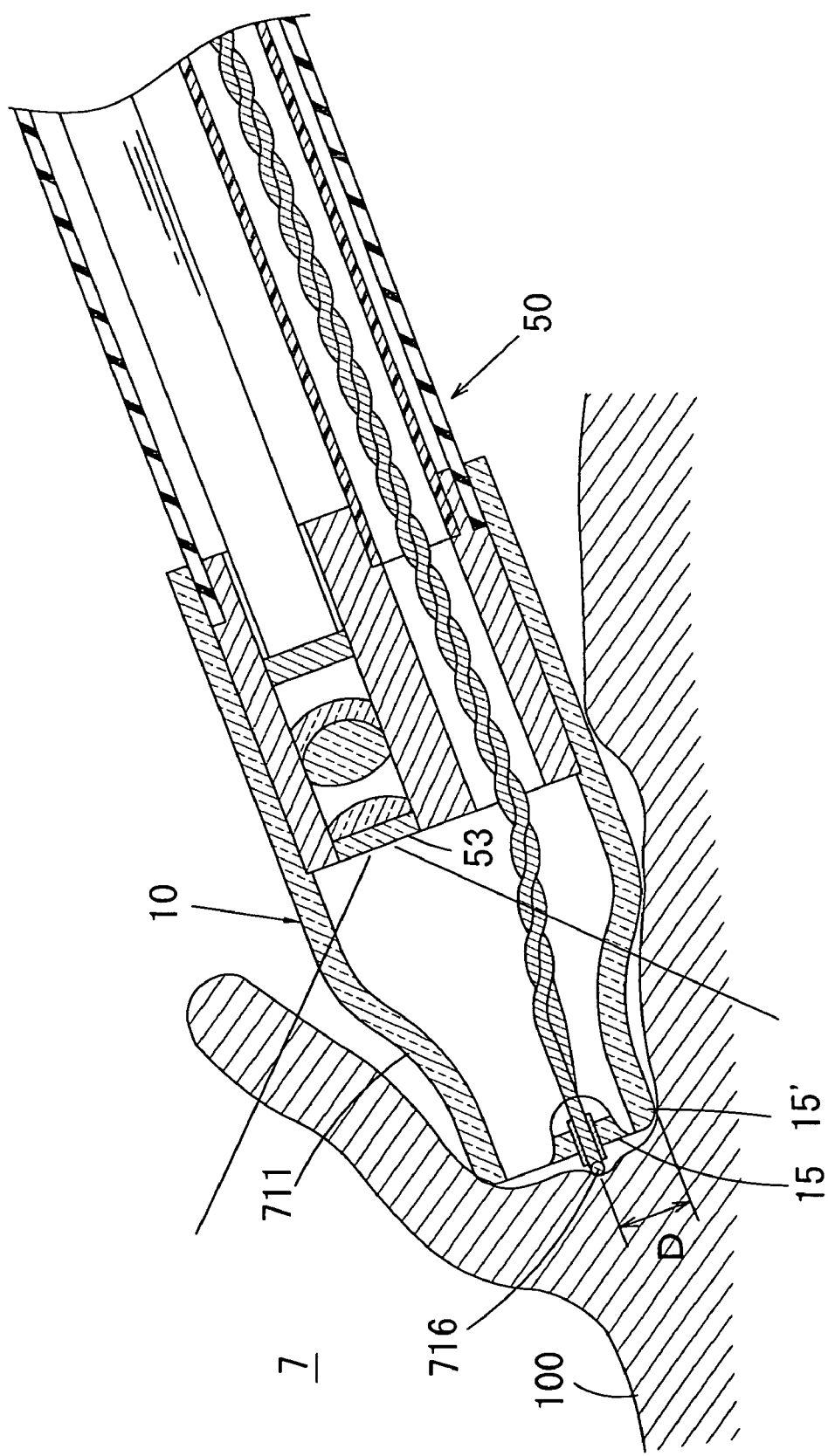
FIG. 28 is a cross sectional view of the seventh embodiment of the endoscopic high-frequency knife, showing an operational state thereof.

FIG. 28 shows an operational state of an endoscopic mucosal resection (EMR) with the use of the seventh embodiment of the endoscopic high-frequency knife 7. In the endoscopic mucosal resection, the high-frequency cutting electrode 716 is pressed against a mucosa of the body tissue 100 and energized to thereby make it possible to dissect the submucosa as shown in FIG. 28.

In such a dissecting operation, the high-frequency cutting electrode 716 does not have to be steered to the affected area independently. Namely, the high-frequency cutting electrode 716 can be steered to a given affected area simply by steering the steerable bendable portion 57 of the endoscope 50. Moreover, one can perform this steering operation while viewing the conditions of the high-frequency cutting electrode 716, and the periphery thereof including dissected surfaces of the submucosa, in real time through the transparent cylindrical projecting portion 711.

During such an operation, the cutting depth by the high-frequency cutting electrode 716 can be easily adjusted remotely by changing the direction of the tip of the insertion portion 58 of the endoscope 50 by manipulating the steerable bendable portion 57. In this manner a sinew between a mucosa and a lamina muscularis which was formerly considered difficult to be cut can be cut with precision to exfoliate the mucosa.

Dissecting a submucosa to an excessive depth can be prevented from occurring by setting a distance D (see FIG. 28) between a lower end point 15' of the front end surface 15 of the cylindrical projecting portion 711 and the high-frequency cutting electrode 716 to an appropriate distance.

[Eighth Embodiment]

Figure 29:
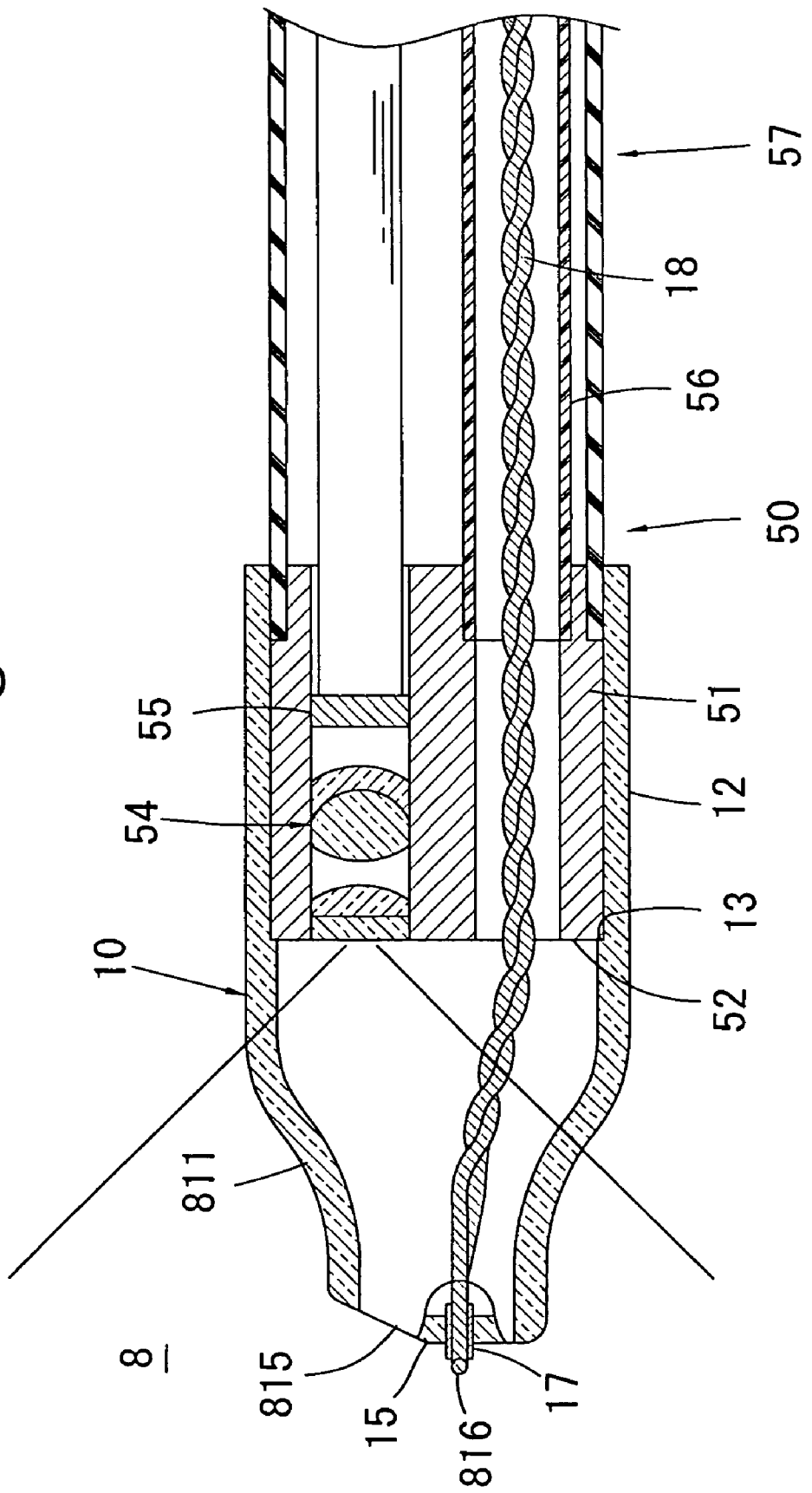
FIG. 29 is a cross sectional view of an eighth embodiment of the endoscopic high-frequency knife according to the present invention, and the distal end of an endoscope to which the endoscopic high-frequency knife is attached.

FIG. 29 shows an eighth embodiment of the endoscopic high-frequency knife 8 according to the present invention. The eighth embodiment is the same as the seventh embodiment of the high-frequency knife except that an upper portion of the front end surface 15 of the cylindrical projecting portion 811 is formed as an oblique surface 815 with the high-frequency cutting electrode 816 being positioned in the vicinity of the front end (crest) of the oblique surface 815 (the bottom end of the oblique surface 815 as viewed in FIG. 29) so that a mucosa, which is dissected by the high-frequency cutting electrode 816, can be easily thrust aside by the front end surface 15 of the cylindrical projecting portion 811 in the eighth embodiment of the endoscopic high-frequency knife 8.

[Ninth Embodiment]

In an endoscopic high-frequency knife 9 of the ninth embodiment, a high-frequency cutting electrode 916 is attached to the transparent hood 10 in a vicinity of a tip of the transparent hood portion 11 to project forward therefrom, and a counter electrode 915 is fixed to an outer peripheral surface of the transparent hood 10. The high-frequency cutting electrode 916 and the counter electrode serve as a pair of high-frequency electrodes.

Figure 30:
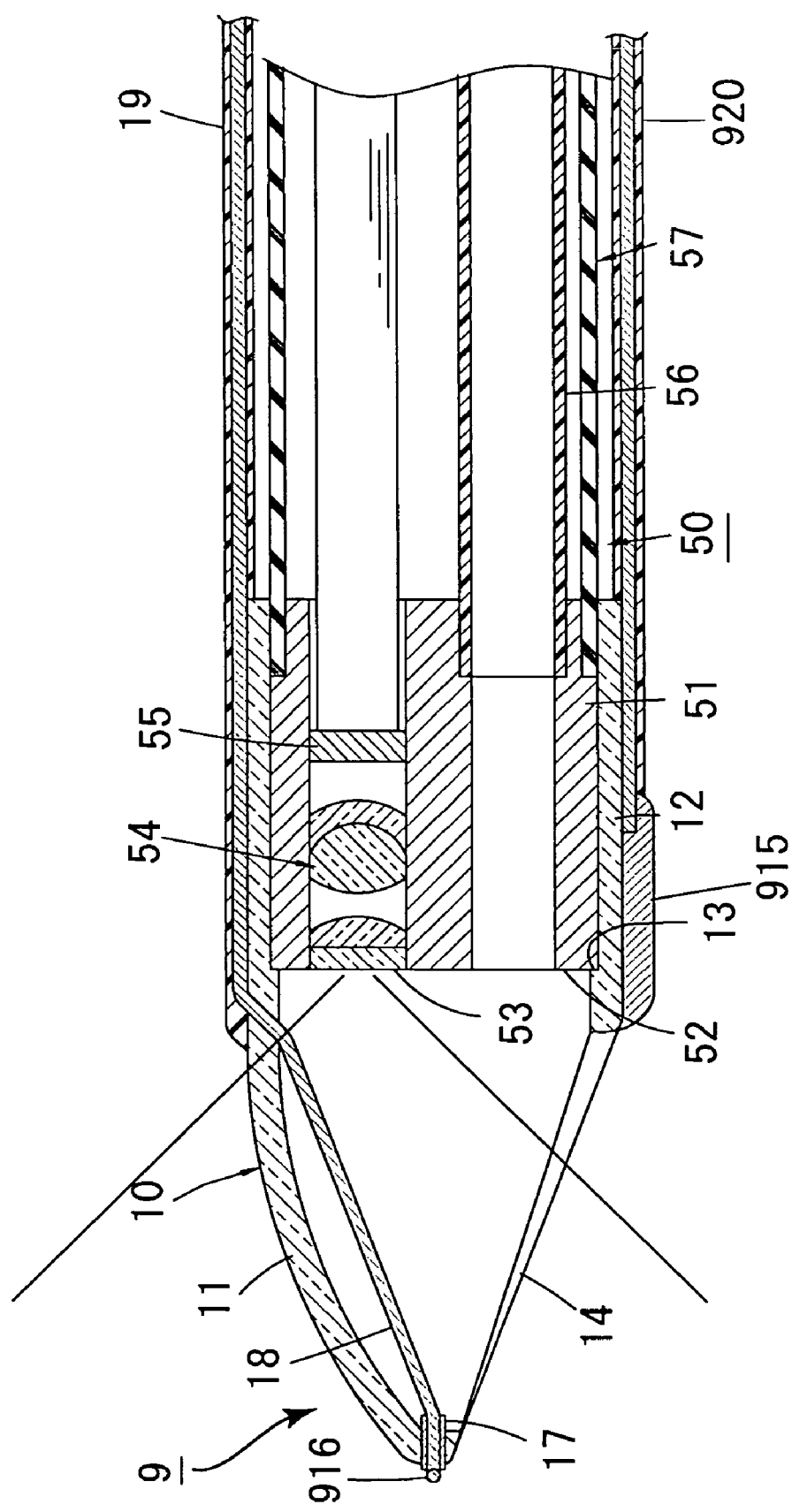
FIG. 30 is a cross sectional view of a ninth embodiment of the endoscopic high-frequency knife according to the present invention, and the distal end of an endoscope to which the endoscopic high-frequency knife is attached.
Figure 31:
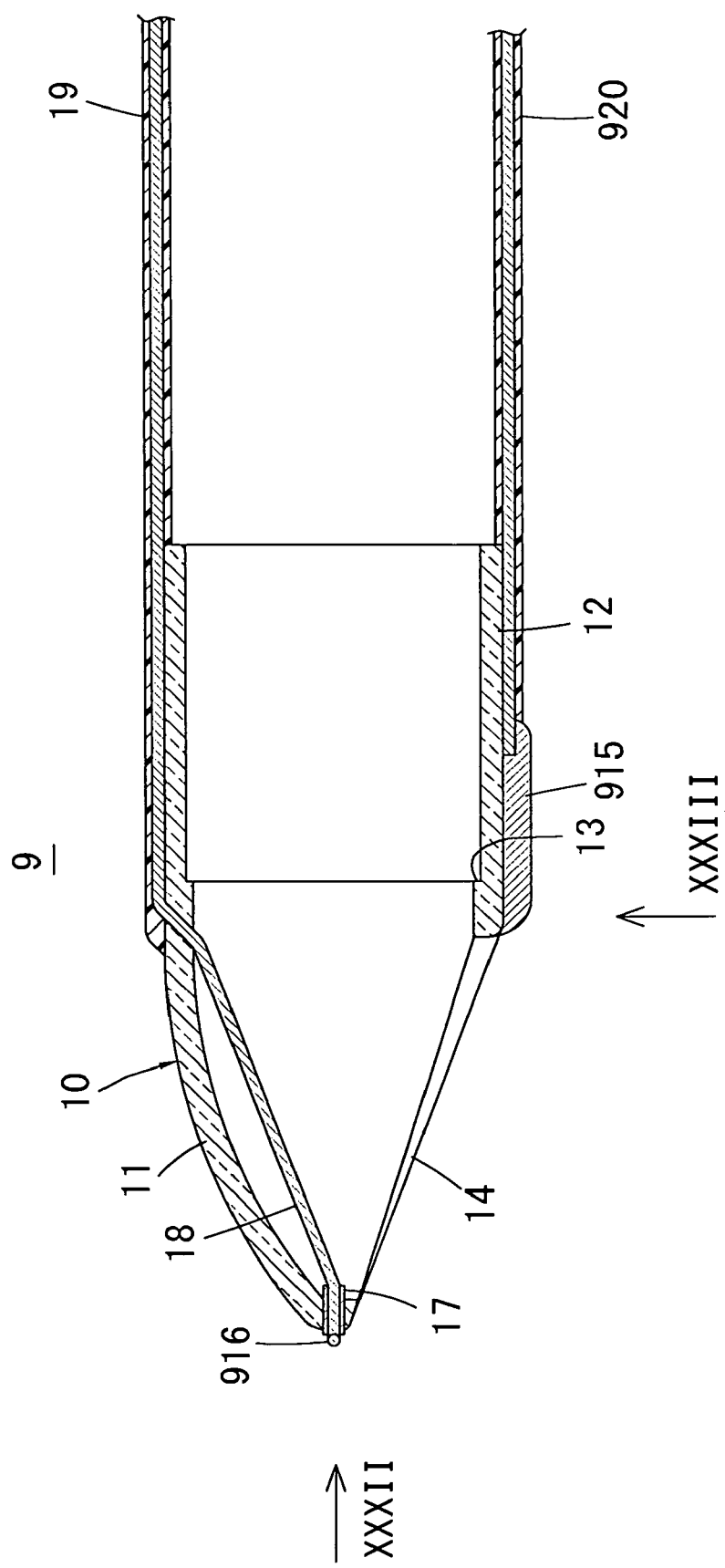
FIG. 31 is a cross sectional view of the ninth embodiment of the endoscopic high-frequency knife shown in FIG. 30.
Figure 32:
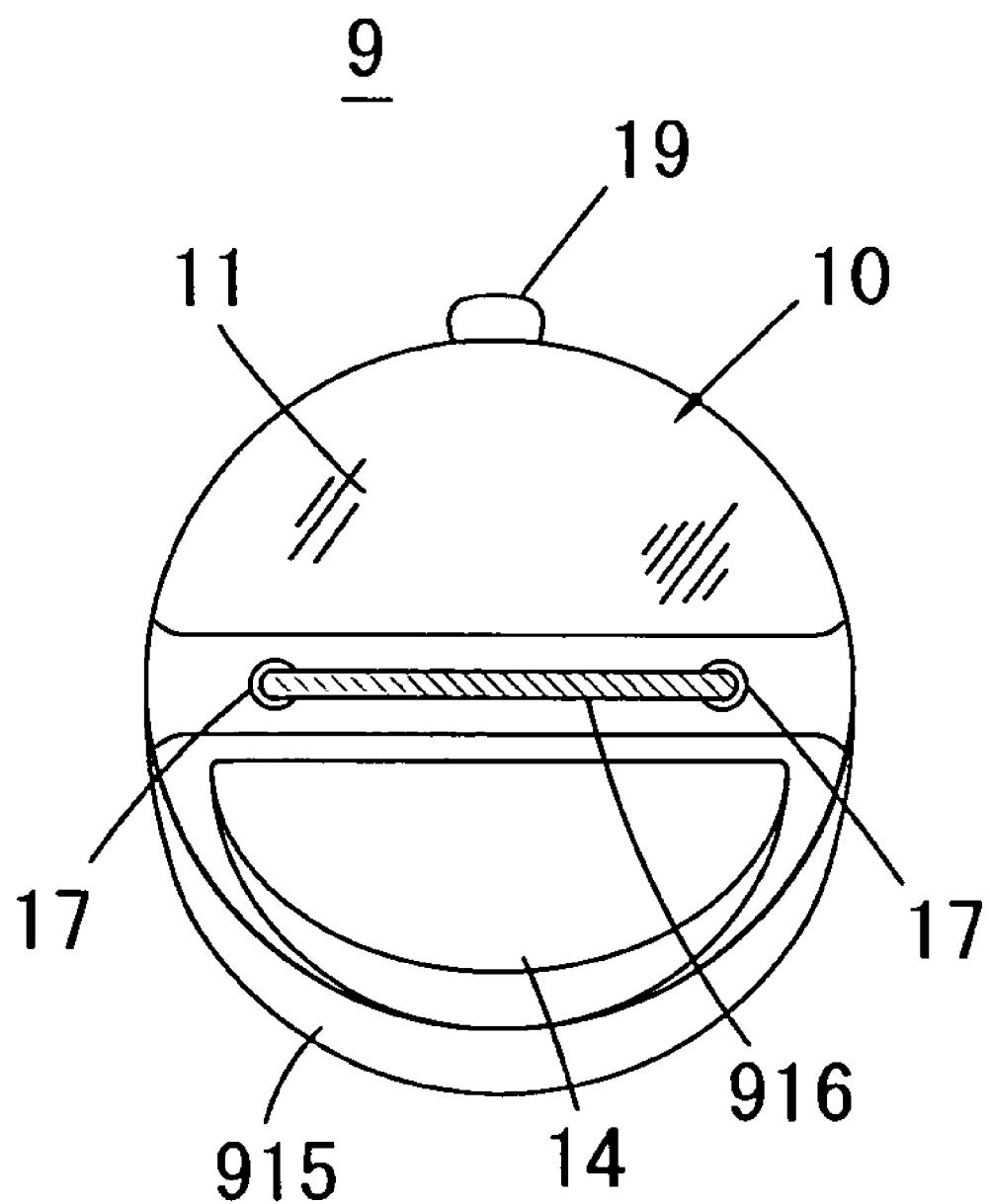
FIG. 32 is a front view of the ninth embodiment of the endoscopic high-frequency knife, viewed in the direction of an arrow XXXII shown in FIG. 31.
Figure 33:
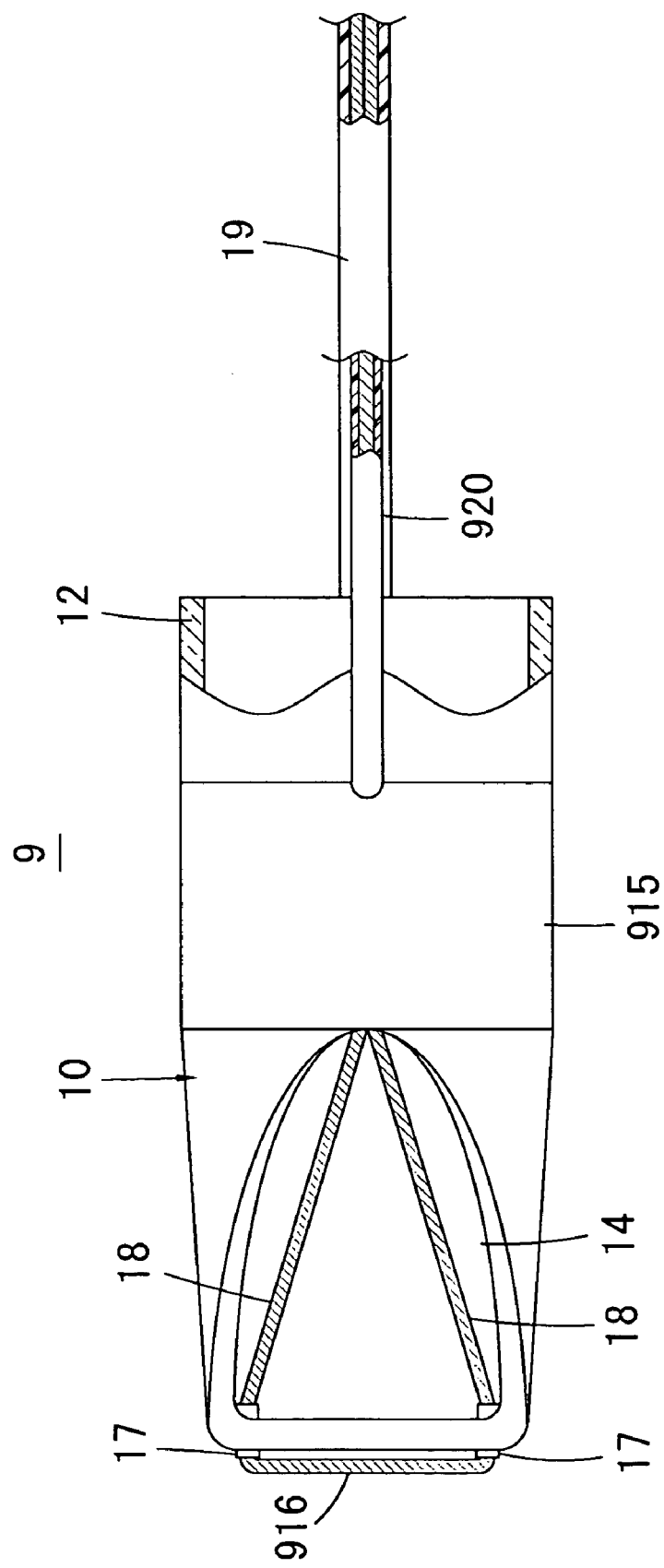
FIG. 33 is a bottom view, partly cross section, of the ninth embodiment of the endoscopic high-frequency knife, viewed in the direction of an arrow XXXIII shown in FIG. 31.

FIG. 30 is a cross sectional view of a ninth embodiment of the endoscopic high-frequency knife 9 according to the present invention, and the distal end of an endoscope 50, showing a state where the endoscopic high-frequency knife 9 is attached to the distal end of the endoscope 50. FIG. 31 is a cross sectional view of the endoscopic high-frequency knife 9, FIG. 32 is a front view of the endoscopic high-frequency knife 9, viewed in the direction of an arrow XXXII shown in FIG. 31, and FIG. 33 is a bottom view, partly cross section, of the endoscopic high-frequency knife 9, viewed in the direction of an arrow XXXIII shown in FIG. 31.

In this embodiment, the hood portion 11 of the transparent hood 10 is formed to have a curved surface which is slightly convexed outwards, similar to the hood portion 11 of the endoscopic high-frequency knife 1 shown in FIG. 1. As shown in FIG. 33, the tip of the hood portion 11 is formed to have a laterally straight surface, to which a high-frequency cutting electrode 916 that serves as a positive electrode of a pair of high-frequency electrodes is attached, to project forward from the laterally straight surface.

The high-frequency cutting electrode 916 is made of a conductive wire. The endoscopic high-frequency knife 9 is provided, at the tip of the hood portion 11 in the vicinity of laterally-opposite ends thereof, with two heat-resistant pipes 17 made of ceramics, respectively, which are positioned laterally apart from each other and each of which penetrates through the tip of the hood portion 11 in a forward/rearward direction of the transparent hood 10. The opposite ends of the high-frequency cutting electrode 916 are inserted into the two heat-resistant pipes 17 from the front ends thereof, respectively, so that the high-frequency cutting electrode 916 is attached to the tip of the hood portion 11 while remaining tight-stretched between the front ends of the two heat-resistant pipes 17.

Two conductive wires 18 which extend from the opposite ends of the high-frequency cutting electrode 916 come out from the rear ends of the two heat-resistant pipes 17, respectively, to be drawn out from the transparent hood 10 in the vicinity of the mounting portion 12 through the space inside the hood portion 11, and are subsequently extended rearward as a positive conductive cable (two-wire cable) 19.

The high-frequency cutting electrode 916 serves as a positive electrode of a pair of high-frequency electrodes, while the endoscopic high-frequency knife 9 is provided immediately behind the opening 14 with a counter electrode 915 which serves as a negative electrode of the pair of high-frequency electrodes and which has a far greater surface area than the high-frequency cutting electrode 916. The counter electrode 915 is attached to an outer peripheral surface of the transparent hood 10, and is formed in a semi-cylindrical shape extending over approximately half of the circumference of the transparent hood 10. The counter electrode 915 extends from a rear end of the hood portion 11 to a center of the cylindrical mounting portion 12 of the transparent hood 10 in the axial direction thereof.

The endoscopic high-frequency knife 9 is provided with a negative-electrode conductive cable 920, a front end of which is connected to the counter electrode 915. The conductive cable 920 extends rearward from the transparent hood 10. As shown in FIG. 32, the high-frequency cutting electrode 916 is positioned to be elongated in a direction substantially parallel to a straight line connecting diametrically opposite ends of the counter electrode 915 which has a semi-circular cross section.

Figure 34:
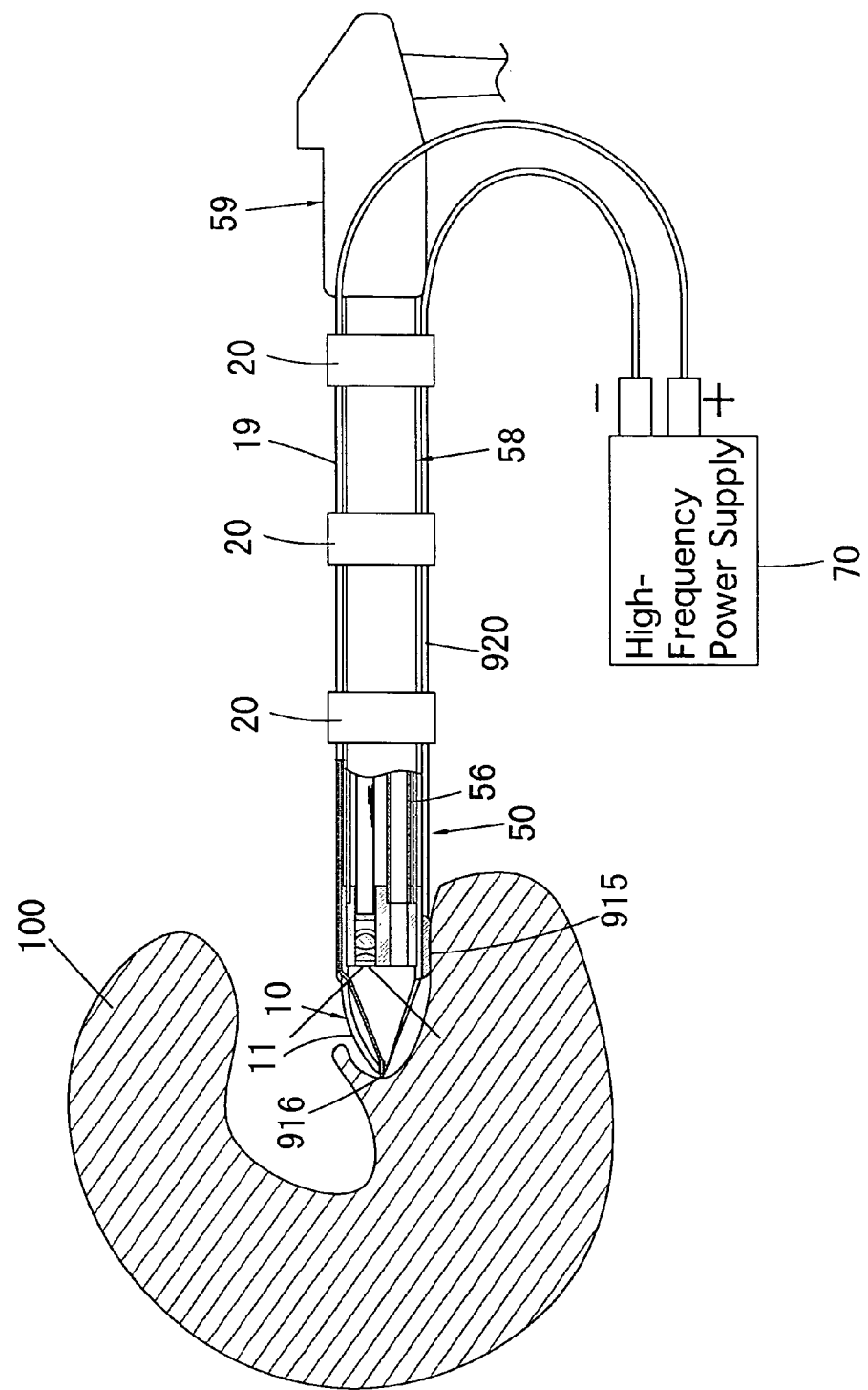
FIG. 34 is a schematic diagram showing a state where the ninth embodiment of the endoscopic high-frequency knife is set to dissect a submucosa of a body tissue with the endoscopic high-frequency knife.

FIG. 34 shows a state where the ninth embodiment of the endoscopic high-frequency knife 9 is set to dissect a submucosa of a body tissue 100 therewith. In this state, the conductive cables 19 and 920 which are drawn from the transparent hood 10 to extend rearward are fixed on an insertion portion 58 of the endoscope 50 along a lengthwise direction thereof by fixing bands 20, so that the rear ends of the conductive cables 19 and 920 are connected to a positive terminal and a negative terminal (output terminals) of a high-frequency power supply 70, respectively. The reference numeral 59 shown in FIG. 34 designates an operational portion of the endoscope 50.

In a dissecting operation with the use of the ninth embodiment of the endoscopic high-frequency knife 9, both the counter electrode 915 and the high-frequency cutting electrode 916 are pressed against a mucosa and energized. At this time, a portion of the mucosa which comes in contact with the counter electrode 915 has a large contacting area and is accordingly influenced little by the passing electric current. Consequently, it is possible for only a portion of the mucosa, which is in contact with the high-frequency cutting electrode 916, to be dissected.

In such a dissecting operation, the high-frequency cutting electrode 916 does not have to be steered to the affected area independently. Namely, the high-frequency cutting electrode 916 can be steered to a given affected area simply by steering the steerable bendable portion 57 of the endoscope 50. Moreover, one can perform this steering operation while viewing the conditions of the high-frequency cutting electrode 916 and its periphery including dissected surfaces of the submucosa in real time through the transparent hood portion 11.

During such an operation, the cutting depth by the high-frequency cutting electrode 916 can be easily adjusted remotely by changing the direction of the tip of the insertion portion 58 of the endoscope 50 by manipulating the steerable bendable portion 57. In this manner a sinew between a mucosa and a lamina muscularis which was formerly considered difficult to be cut can be cut with precision to exfoliate the mucosa.

Thereafter, if necessary, various kinds of additional endoscopic operations to the body tissue 100 can be performed with the use of various endoscopic treatment tools (not shown) which are used by being introduced into the body through the treatment tool insertion channel 56 of the endoscope 50 to gain therapeutic effect.

[Tenth Embodiment]

FIG. 35 is a cross sectional view of a tenth embodiment of the endoscopic high-frequency knife 10, according to the present invention, and the distal end of an endoscope 50, showing a state where the endoscopic high-frequency knife 10 is attached to the distal end of the endoscope 50. FIG. 36 is a bottom view of the tenth embodiment of the endoscopic high-frequency knife 10 shown in FIG. 35. This embodiment of the endoscopic high-frequency knife 10 is substantially the same as the ninth embodiment of the endoscopic high-frequency knife 9 shown in FIGS. 30 through 34 except for several parts which will be discussed hereinafter. In the tenth embodiment of the endoscopic high-frequency knife 10, the conductive cables 19 and 200 are integrated in the endoscope 50, and a positive contact 19*a* connected to the front end of the conductive cable 19 and a negative contact 1020 connected to the front end of the conductive cable 200 are positioned on an outer peripheral surface of the distal end member 51 in the vicinity of the front end thereof.

To align the positions of the positive contact 19*a* and the negative contact 1020 so as to correspond with each other, a cutting-electrode contact 1016*a* and a counter-electrode contact 1015*a* which respectively come into contact with the positive contact 19*a* and the negative contact 1020 upon the transparent hood 10 being attached to the cylindrical distal end member 51 are fixedly positioned radially inside the mounting portion 12 of the transparent hood 10. The cutting-electrode contact 1016*a* is connected to an end of the conductive wire 18, the other end of which is connected to the high-frequency cutting electrode 1016, while the counter-electrode contact 1015*a* is connected to a counter electrode 1015 which corresponds to the counter electrode 150.

Due to this structure, the cutting-electrode contact 1016*a* and the counter-electrode contact 1015*a* come into contact with the positive contact 19*a* and the negative contact 1020, respectively, upon the transparent hood 10 being attached to the distal end member 51 of the endoscope 50. Accordingly, the tenth embodiment of the endoscopic high-frequency knife 10 is easy -to handle because neither of the conductive cables 19 and 200 extend outwards from the transparent hood 10.

Additionally, the counter electrode 1015 is attached to an outer peripheral surface of the transparent hood 10, and is formed in a cylindrical shape which circumferentially surrounds the transparent hood 10, while the high-frequency cutting electrode 1016 is shaped to project forward from the tip of the hood portion 11 as shown in FIG. 36. This structure makes it easy for each of the counter electrode 1015 and the high-frequency cutting electrode 1016 to be brought into contact with a mucosa of the body tissue 100.

As can be understood from the foregoing, according to the present invention, one can easily and safely dissect a medically-optimum prescribed area of submucosa, and the like, due to the dissected surfaces of the submucosa, and the like, being able to be viewed in real time while being dissected by the high-frequency cutting electrode. Moreover, in such a dissecting operation, the high-frequency cutting electrode does not have to be steered to the affected area independently; namely, the high-frequency cutting electrode can be steered to a given affected area simply by steering the endoscope. Therefore, such a dissecting operation can be easily performed by a simple operation of the endoscope.

Obvious changes may be made in the specific embodiment of the present invention described herein, such modifications being within the spirit and scope of the invention claimed. It is indicated that all matter contained herein is illustrative and does not limit the scope of the present invention.

What is claimed is:

1. An endoscopic high-frequency knife comprising:
a hood which is mounted to a distal end member fixed at a distal end of an endoscope to surround an end surface of said distal end member, an objective window being positioned on said end surface of said distal end member;

a transparent hood portion which is formed on said hood to project forward from a portion of said hood in a vicinity of said end surface while being gradually curved inwards so as to cover the front of said end surface in a direction away from said end surface; and a high-frequency cutting electrode comprising a conductive wire having opposite ends and attached to said hood in a vicinity of a tip of said transparent hood portion via at least two ceramic pipes, each of said opposite ends attached to a respective pipe of said at least two ceramic pipes, said high-frequency cutting electrode projecting forward from said transparent hood portion.

2. The endoscopic high-frequency knife according to claim 1, wherein said hood is detachably attached to said distal end member.

3. The endoscopic high-frequency knife according to claim 1, wherein said high-frequency cutting electrode extends linearly between said two separate points.

4. The endoscopic high-frequency knife according to claim 1, wherein said hood comprises a mounting portion which is mounted to said distal end member when said hood is attached to said distal end member, and wherein a second conductive wire which extends from an end of said conductive wire is drawn out from said hood in a vicinity of said mounting portion of said hood through a space inside said transparent hood portion.

5. The endoscopic high-frequency knife according to claim 1, wherein said conductive wire is drawn out from a rear end of said hood to extend rearward through a space inside said transparent hood portion.

6. The endoscopic high-frequency knife according to claim 1, wherein said hood has an opening on the opposite side of said hood from said transparent hood portion, said opening being shaped in such a manner that a portion of said hood between a point on said hood in a vicinity of a tip thereof and a point on a mounting portion of said hood that is mounted to said distal end member is cut off.

7. The endoscopic high-frequency knife according to claim 6, wherein said opening is positioned in front of said end surface of said distal end member, and is shaped in such a manner that said portion of said hood is obliquely cut off.

8. The endoscopic high-frequency knife according to claim 6, wherein said transparent hood portion is shaped to fully cover the front of said end surface of said distal end member.

9. The endoscopic high-frequency knife according to claim 1, wherein said endoscope comprises an objective optical system provided behind said objective window.

10. The endoscopic high-frequency knife according to claim 1, wherein said hood is made of a transparent material.

11. The endoscopic high-frequency knife according to claim 1, wherein said opposite ends of said conductive wire project through respective front ends of said two ceramic pipes such that the high-frequency cutting electrode is positioned at the tip of said hood portion and is stretched between said front ends of said two ceramic pipes.

12. An endoscopic high-frequency knife comprising:

a hood which is mounted to a distal end member fixed at a distal end of an endoscope to surround an end surface of said distal end member, an objective window being positioned on said end surface of said distal end member;

a transparent projecting portion which is formed on said hood to project forward from a portion of said hood in a vicinity of said end surface; and a high-frequency cutting electrode comprising a conductive wire having opposite ends and attached to said hood in a vicinity of a tip of said transparent projecting portion via at least two ceramic pipes, each of said opposite ends attached to a respective pipe of said at least two ceramic pipes to project outwards therefrom.

13. The endoscopic high-frequency knife according to claim 12, wherein said hood comprises a mounting portion which is mounted to said distal end member when said hood is attached to said distal end member, and wherein a second conductive wire which extends from an end of said conductive wire is drawn out from said hood in a vicinity of said mounting portion of said hood through a space inside said transparent projecting portion.

14. The endoscopic high-frequency knife according to claim 12, wherein said opposite ends of said conductive wire project through respective front ends of said two ceramic pipes such that said high-frequency cutting electrode is positioned at the tip of said hood portion and is stretched between said front ends of said two ceramic pipes.

* * * * *